US007485745B2

(12) United States Patent
Maas et al.

(10) Patent No.: US 7,485,745 B2
(45) Date of Patent: *Feb. 3, 2009

(54) MIXTURES COMPOSED OF MONOCARBOXY-FUNCTIONALIZED DIALKYLPHOSPHINIC ESTERS AND OF FURTHER COMPONENTS

(75) Inventors: Wiebke Maas, Huerth (DE); Werner Krause, Huerth (DE); Harald Bauer, Kerpen (DE)

(73) Assignee: Clariant International Ltd., Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/714,481

(22) Filed: Mar. 6, 2007

(65) Prior Publication Data
US 2007/0210288 A1   Sep. 13, 2007

(30) Foreign Application Priority Data
Mar. 7, 2006 (DE) ........................ 10 2006 010 361

(51) Int. Cl.
C07F 9/22 (2006.01)
(52) U.S. Cl. ........................................................ 562/24
(58) Field of Classification Search .................... 562/24
See application file for complete search history.

(56) References Cited

U.S. PATENT DOCUMENTS

| 2,279,501 | A | * | 4/1942 | Dickey et al. ................ 428/393 |
| 2,579,810 | A | * | 12/1951 | Fields .......................... 558/135 |
| 2,957,931 | A |   | 10/1960 | Hamilton et al. |
| 3,021,279 | A | * | 2/1962 | Scanley ........................ 507/237 |
| 3,178,469 | A | * | 4/1965 | Fields .......................... 558/129 |
| 3,974,243 | A | * | 8/1976 | Kleiner ......................... 558/198 |
| 4,018,854 | A | * | 4/1977 | McIntosh ..................... 558/181 |
| 4,020,101 | A | * | 4/1977 | Geffers et al. ................. 562/24 |
| 4,088,677 | A | * | 5/1978 | Kleiner ......................... 562/24 |
| 4,560,518 | A |   | 12/1985 | Gehrmann et al. |
| 4,830,764 | A |   | 5/1989 | Wiedemann |
| 5,376,731 | A | * | 12/1994 | Kerr et al. .................... 525/340 |
| 6,090,967 | A |   | 7/2000 | Horold et al. |
| 6,090,976 | A | * | 7/2000 | Kim et al. ..................... 562/24 |
| 6,204,420 | B1 |   | 3/2001 | Miller et al. |
| 6,278,012 | B1 |   | 8/2001 | Horold et al. |
| 6,355,832 | B1 | * | 3/2002 | Weferling et al. ............. 562/8 |
| 6,534,673 | B1 | * | 3/2003 | Weferling et al. ............. 562/8 |
| 6,770,779 | B1 |   | 8/2004 | Weferling et al. |
| 6,855,757 | B2 |   | 2/2005 | Horold et al. |
| 7,129,320 | B2 | * | 10/2006 | Sicken et al. ................. 528/398 |
| 7,148,276 | B2 | * | 12/2006 | Bauer et al. ................... 524/126 |
| 2003/0171466 | A1 |   | 9/2003 | Horold et al. |
| 2005/0101704 | A1 | * | 5/2005 | Eisentraeger et al. ....... 524/100 |
| 2005/0101706 | A1 | * | 5/2005 | Bauer et al. ................... 524/115 |
| 2005/0137418 | A1 | * | 6/2005 | Bauer et al. ................... 562/8 |
| 2005/0143503 | A1 | * | 6/2005 | Bauer et al. ................... 524/115 |
| 2006/0074157 | A1 | * | 4/2006 | Bauer et al. ................... 524/115 |
| 2006/0084734 | A1 | * | 4/2006 | Bauer et al. ................... 524/115 |
| 2006/0214144 | A1 | * | 9/2006 | Bauer et al. ................... 252/609 |
| 2006/0217469 | A1 | * | 9/2006 | Bauer et al. ................... 524/115 |
| 2006/0226404 | A1 | * | 10/2006 | Bauer et al. ................... 252/601 |
| 2006/0287418 | A1 | * | 12/2006 | Bauer et al. ................... 524/127 |
| 2007/0027297 | A1 | * | 2/2007 | Sicken et al. ................. 528/398 |
| 2007/0213436 | A1 | * | 9/2007 | Maas et al. ................... 524/133 |

FOREIGN PATENT DOCUMENTS

| DE | 3245364 | 6/1984 |
| DE | 10153780 | 11/2002 |
| EP | 0063896 | 11/1982 |
| JP | 07102418 | 4/1995 |

OTHER PUBLICATIONS

U.S. Appl. No. 11/714,482, filed Mar. 6, 2007 by Wiebke Maas et al.
U.S. Appl. No. 11/714,331, filed Mar. 6, 2007 by Wiebke Maas.
V.K. Chajrullen, R.R. Shagidullin, Z. Obschei Khim. 36 pp. 289-302 (1966).
K. Sasse, "Phosphinsauren und deren Derivate," Houben-Weyl, vol. 12/1, pp. 258-259 (1963).

(Continued)

Primary Examiner—Daniel M Sullivan
Assistant Examiner—Louisa Lao
(74) Attorney, Agent, or Firm—Anthony A. Bisulca

(57) ABSTRACT

The invention relates to mixtures composed of dialkylphosphinic esters and of further components, which comprise
A) from 98 to 100% by weight of monocarboxy-functionalized dialkylphosphinic esters of the formula (I)

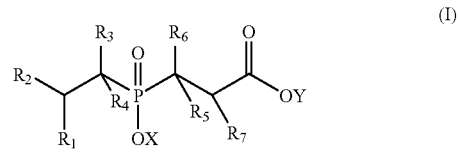

(I)

in which $R_1$, $R_2$, $R_3$, $R_4$, $R_5$, $R_6$, and $R_7$ are identical or different and, independently of one another, are H, methyl, ethyl, n-propyl, isopropyl, n-butyl, isobutyl, tert-butyl, and/or phenyl, Y is methyl, ethyl, n-propyl, isopropyl, n-butyl, isobutyl, tert-butyl, phenyl, 2-hydroxyethyl, 2,3-dihydroxypropyl, 2-hydroxypropyl, 3-hydroxypropyl, 4-hydroxybutyl, 3-hydroxybutyl, 2-hydroxybutyl, and/or 6-hydroxyhexyl, allyl, and/or glycerol, X is H, Li, Na, K or $NH_4$, or X is defined as for Y, and then X and Y are two identical radicals or two different radicals of the above organic radicals, and B) from 0 to 2% by weight of halogens, where the entirety of the components always amounts to 100% by weight.

15 Claims, No Drawings

OTHER PUBLICATIONS

K. Sasse, "Phosphonigo Sauren und deren Derivato," Houben-Weyl, vol. 12/1, p. 306 (1966).

Kurdyumova, N.R. et al. Synthisis of Phosphonic Acids from Hypophosphites I. Acrylates as an Unsaturated Component; Russian Journal of General Chemistry, vol. 67. No. 12, pp. 1852-1856 (1997).

German Search Opinion for 102006010361.0 mailed Oct. 23, 2006.

English Abstract for JP 07102418, Apr. 18, 1995.

EPO Search Report for EP 07004233, Jul. 3, 2007.

Khalrullln et al., "Reaction of ethyl- and toyldichlorophosphine with alpha, beta-unsaturated acids" Zhurnal Obshchel Khimii, 37(8), pp. 1838-1843 XP 00908471 (1967) and English Abstract thereof.

Khairullin et al., "Reaction of ethylphosphonous dichloride with crotonic acid" Zhurnal Obshchei Khimii, 36(3), pp. 494-498 (1966), XP 009084872 and English Abstract thereof.

Pudovik et al., "New Method of Synthesis of Esters of Phosphonic and Thlophosphonic Esters. XVI Synthesis of Esters of Mono- and diphosphono—and thiophosphonocarboxylic acids" Bulletin of the Academy of the USSR, Division of Chemical Science (English Translation) pp. 543-550, XP 09084884 (1954).

Pudovik et al., "New Method of Synthesis of Esters of Phosphonic and Thlophosphonic Esters. XVI Synthesis of Esters of Mono- and diphosphono—and thiophosphonocarboxylic acids" Izvestiya Akademii Nauk USSR, Seriya Khimicheskaya, pp. 636-645, XP 009084884 (1954) and English Abstract thereof.

Pudovik et all., "Reaction of 2-ethyl-2,5-dioxo-1,2-oxaphospholane with aicohols," Zhurnal Obshchei Khimii, 52(4), pp. 786-789. XP009084875 (1982) and English Abstract thereof.

Pudovik et al., "Reaction of phosphorus (III) acid chlorides with carboxylic acids," Khim. Elementoorg. Soedin, pp. 156-160, XP 009084876 (1976) and English Abstract thereof.

Khairullin et al., "Reaction of ethyldichlorophosphine with acrylic acid esters" Izvestiya Alkademii Nauk SSSR, Seriya Khimicheskaya, (4) pp. 871-876, XP 009084869 (1970).

Khairullin et al., "Synthesis and Some Properties of ethyl [.beta.-(ethoxycarbonyl) ethyl] phosphinyl chloride," Zhurnal Obschei Khimii, 39(2), pp. 341-346, XP 009084870 (1969) and English Abstract thereof.

Bertenshaw et al., "Phosphorus—containing Ihnhibitors of Endothelin Converting Enzyme: Effects of the Electronic Nature of Phosphorus on Inhibitor Potency," Journal of Medicinal Chemistry, American Chemical Society, Washington, D.C., Bd. 36, Nr. 1, pp. 173-176 XP 001180518 (1993).

Grobelny et al., "Binding Energetics of Phosphorus containing Inhibitors of Thermolysin," Biochemistry, American Chemical Society, Easton, PA, US Bd. 28, Hr.12, pp. 4948-4951 XP 000009206 (Jun. 1, 1989).

Tsivunin et al., "Reactions of some phosphorus acids with .alpha, .beta—unsaturated acid halides," Zhurnal Obshchei Khimii, 40(9) pp. 1995-2001, XP 009084873 (1970).

Pudovik et al., "New synthesis of esters of phosphonic and thiophosphonic acids. XV addition of esters of phenyl and alkylphosphonous acids to esters of methacrylic and acrylic acids," Izvestiya Akademii Nauk SSSR, Serlya Khimicheskaya pp. 902-907; XP 009084883 (1952) and English Abstract thereof.

\* cited by examiner

MIXTURES COMPOSED OF MONOCARBOXY-FUNCTIONALIZED DIALKYLPHOSPHINIC ESTERS AND OF FURTHER COMPONENTS

The present invention is described in the German priority application No. 10 2006 010 361.0, filed Jul. 3, 2006, which is hereby incorporated by reference as is fully disclosed herein.

The invention relates to mixtures composed of monocarboxy-functionalized dialkylphosphinic esters and of further components, to their use, and to a process for their preparation.

Monocarboxy-functionalized dialkylphosphinic esters and their derivatives are known. They can be prepared by various processes.

There are many descriptions of a process in which the monocarboxy-functionalized dialkylphosphinic ester is prepared by way of a plurality of steps starting from phosphonous dihalides. Among these are the reaction of dihalophosphines with activated olefinic compounds, e.g. acrylic acid, followed by esterification of the initially formed acid chloride derivatives and anhydride derivatives with alcohols (V. K. Khairullin, R. R. Shagidullin, Zh. Obshch. Khim. 36, 289-296).

Monocarboxy-functionalized dialkylphosphinic esters are also obtained when phosphonous monoesters undergo an addition reaction with α,β-unsaturated carboxylic esters in the presence of peroxidic catalysts (Houben-Weyl, volume 12/1, pp. 258-259). The phosphonous monoesters themselves are in turn prepared from phosphonous dihalides via reaction with alcohols or via hydrolysis and subsequent esterification.

The abovementioned phosphonous dihalides themselves have hitherto been prepared in a complicated synthesis from phosphorus trichloride and alkyl chloride in the presence of aluminum chloride (Houben-Weyl, volume 12/1, p. 306). The reaction is highly exothermic and difficult to control in an industrial context. Furthermore, various by-products are formed which, like some of the abovementioned starting materials, are toxic and/or corrosive, i.e. highly undesirable. Another known process for preparation of monocarboxy-functionalized dialkylphosphinic esters is based on the reaction of yellow phosphorus with methyl chloride, giving methylphosphonous acid, which is then esterified and then reacted with acrylic ester (DE-A-101 53 780).

Monocarboxy-functionalized dialkylphosphinic esters can also be obtained via reaction of bis(trimethylsilyl)phosphonite —HP(OSiMe$_3$)$_2$— with α,β-unsaturated carboxylic acid components, subsequent alkylation with alkyl halides in the Arbuzov reaction and alcoholysis (Kurdyumova, N. R.; Rozhko, L. F.; Ragulin, V. V.; Tsvetkov, E. N.; Russian Journal of General Chemistry (Translation of Zhurnal Obshchei Khimii (1997), 67(12), 1852-1856). The bis(trimethylsilyl) phosphonite here is obtained from potassium hypophosphite or ammonium hypophosphite via reaction with hexamethyldisilazane.

The abovementioned processes use large amounts of halogen-containing chemicals. The resultant monocarboxy-functionalized dialkylphosphinic esters therefore comprise halogen-containing by-products.

The synthesis-related formation of these halogen-containing by-products is a disadvantage of this prior art, because halogen-containing compounds, in particular chlorine-containing compounds, are known to be more corrosive than halogen-free compounds. Another disadvantage of halogen-containing compounds in relation to their use as flame retardant is that in the event of a fire corrosive and toxic gases can form, making the use of these compounds as flame retardants at least questionable, if not impossible. Downstream removal of the halogen-containing compounds from the products of the processes mentioned generates additional costs for energy and time, with consequent disadvantages in terms of cost-effectiveness and environmental technology.

Among the phosphonic dihalides most frequently used is methyldichlorophosphine, which in turn has hitherto been prepared by a very complicated synthesis from phosphorus trichloride and methyl chloride in the presence of aluminum chloride (Houben-Weyl, volume 12/1, p. 306). The reaction is highly exothermic and is difficult to control under industrial conditions. Furthermore, various by-products, in particular halogen-containing by-products, are formed, and these, like some of the abovementioned starting materials themselves, are toxic and/or corrosive, i.e. highly undesirable. The use of these starting materials and the by-products obtained therefrom is undesirable in view of corrosion and environmental incompatibility.

There is therefore a need for monocarboxy-functionalized dialkylphosphinic esters which have low halogen content or indeed are halogen-free.

There is also a need for a process for preparation of monocarboxy-functionalized dialkylphosphinic esters which can be carried out in a simple and cost-effective manner with little or no use of halogen and which gives unitary products in high yield and purity. This process should also be markedly superior to those known hitherto in terms of environmental technology.

Another object of the invention is therefore to provide a process which can prepare monocarboxy-functionalized dialkylphosphinic acids and which avoids the abovementioned disadvantages of the prior art, and which starts from hypophosphorous acid or from its salts.

However, a first object of the present invention is to provide monocarboxy-functionalized dialkylphosphinic esters which have extremely low halogen content or are halogen-free.

The invention understands halogen-containing compounds to be chemical compounds in which atoms of the 7th main group, in particular fluorine, chlorine, bromine, and iodine, are present and have chemical bonding to carbon or to phosphorus. The invention also understands halogen-containing compounds to be salts which contain halide anions.

This object is achieved via mixtures composed of monocarboxy-functionalized dialkylphosphinic esters and of further components, which comprise A) from 98 to 100% by weight of monocarboxy-functionalized dialkylphosphinic acids of the formula (I)

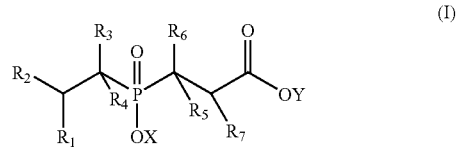

in which $R_1$, $R_2$, $R_3$, $R_4$, $R_5$, $R_6$, and $R_7$ are identical or different and, independently of one another, are H, methyl, ethyl, n-propyl, isopropyl, n-butyl, isobutyl, tert-butyl, and/or phenyl, Y is methyl, ethyl, n-propyl, isopropyl, n-butyl, isobutyl, tert-butyl, phenyl, 2-hydroxyethyl, 2,3-dihydroxypropyl, 2-hydroxypropyl, 3-hydroxypropyl, 4-hydroxybutyl, 3-hydroxybutyl, 2-hydroxybutyl, and/or 6-hydroxyhexyl, allyl, and/or glycerol, X is H, Li, Na, K or NH$_4$,
or X is defined as for Y, and then X and Y are two identical radicals or two different radicals of the above organic radicals, and B) from 0 to 2% by weight of halogens, where the entirety of the components always amounts to 100% by weight.

The mixtures preferably comprise from 99.9995 to 100% by weight of monocarboxy-functionalized dialkylphosphinic esters of the formula (I) and from 0 to 0.0005% by weight of halogens.

The monocarboxy-functionalized dialkylphosphinic ester is preferably methyl 3-(ethylhydroxyphosphinyl)propionate, 2-hydroxyethyl 3-(ethylhydroxyphosphinyl)propionate, 2,3-dihydroxypropyl 3-(ethylhydroxyphosphinyl)propionate, allyl 3-(ethylhydroxyphosphinyl)-2-methylpropionate, 4-hydroxybutyl 3-(ethylhydroxyphosphinyl)-2-methylpropionate, 6-hydroxyhexyl 3-(ethylhydroxyphosphinyl)propionate, 2-hydroxyethyl 3-(ethyl-n-butoxyphosphinyl) isobutyrate, butyl 3-(ethyl-n-butoxyphosphinyl)propionate, methyl 3-(ethylmethoxyphosphinyl)propionate, butyl 3-(propylhydroxyphosphinyl)propionate, 2-hydroxyethyl 3-(propylhydroxyphosphinyl)propionate, 2-hydroxypropyl 3-(propylhydroxyphosphinyl)propionate, 2-hydroxypropyl 3-(propylhydroxyphosphinyl)-2-methylpropionate, methyl 3-(propylhydroxyphosphinyl)propionate, 2-hydroxyethyl 3-(butylhydroxyphosphinyl)propionate, 3-hydroxypropyl 3-(hexylhydroxyphosphinyl)propionate, 2-hydroxyethyl 3-(ethylhydroxyphosphinyl)-2-methylbutyrate, 2-hydroxyethyl 3-(propylhydroxyphosphinyl)-2-methylbutyrate, 2-hydroxypropyl 3-(ethylhydroxyphosphinyl)-2-methylbutyrate, 2-hydroxypropyl 3-(propylhydroxyphosphinyl)-2-methylbutyrate, 2,3-dihydroxypropyl 3-(propylhydroxyphosphinyl)propionate, and/or methyl 3-(ethylmethoxyphosphinyl)-2-methylbutyrate.

The invention also provides a process for preparation of mixtures as claimed in one or more of claims 1 to 3, which comprises reacting hypophosphorous acid or its salts (component C) of the formula II

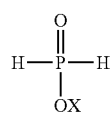

in which X is H, Na, K, or NH$_4$ in the presence of a free-radical initiator with an α,β-unsaturated carboxylic acid derivative (component D) of the formula III,

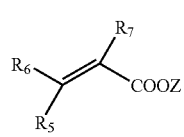

in which Z is C$_{1-18}$-alkyl or C$_{6-18}$-aryl or is Y, or with an α,β-unsaturated carboxylic acid (component D') of the formula IV

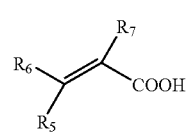

and with an olefin (component E) of the formula V

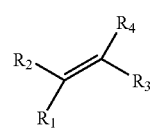

where R$_1$, R$_2$, R$_3$, R$_4$, R$_5$, R$_6$, and R$_7$ are defined in the formulae III, IV, and V as in formula I, and when formula IV is used an esterification step with Y—OH follows.

It is preferable here that, in a step 1, component C is reacted in the presence of a free-radical initiator with component E to give an alkylphosphonous acid and, in step 2, the resultant reaction solution is esterified with an alcohol M-OH and phosphonous ester produced here is removed by distillation and then, in a step 3, is reacted in the presence of a free-radical initiator or of a basic initiator with component D to give the monocarboxy-functionalized dialkylphosphinic ester.

It is preferable here that, in a step 1, component C is reacted in the presence of a free-radical initiator with component E to give an alkylphosphonous acid and, in step 2, the resultant reaction solution is esterified with an alcohol M-OH, and phosphonous ester produced here is removed by distillation and then, in step 3, is reacted in the presence of a free-radical initiator or of a basic initiator with component D' to give the monocarboxy-functionalized dialkylphosphinic ester, where X=alkyl, Y=H, and then, in a step 4, this dialkylphosphinic ester is esterified with an alcohol Y—OH at the carboxy function, giving a monocarboxy-functionalized dialkylphosphinic ester.

It is preferable in this process that, in step 2, the alkylphosphonous acid is directly esterified with a linear or branched alcohol of the formula M-OH, where M is a linear or branched alkyl radical having from 1 to 10 carbon atoms.

It is preferable that the alcohol M-OH is n-butanol, isobutanol or ethylhexanol.

It is preferable that component C is the ammonium or sodium salt of hypophosphorous acid.

It is preferable that the initiator is a free-radical, anionic, cationic, or photochemical initiator.

It is preferable that the initiator is peroxide-forming compounds and/or peroxo compounds, e.g. hydrogen peroxide, sodium peroxide, lithium peroxide, potassium persulfate, sodium persulfate, ammonium persulfate, sodium peroxodisulfate, potassium peroxoborate, peracetic acid, benzoyl peroxide, di-tert-butyl peroxide, and/or peroxodisulfuric acid, and/or is azo compounds, e.g. azodiisobutyronitrile, 2,2'-azobis(2-amidinopropane) dihydrochloride and/or 2,2'-azobis (N,N'-dimethyleneisobutyramidine) dihydrochloride.

It is preferable that the α,β-unsaturated carboxylic acids are acrylic acid, methyl acrylate, ethyl acrylate, methacrylic acid, hydroxyethyl acrylate, crotonic acid, ethyl crotonate, tiglic acid (trans-2,3-dimethylacrylic acid), and/or (trans)-2-pentenoic acid.

It is preferable that the olefin (component E) is ethylene, propylene, n-butene, and/or isobutene, or any desired mixture thereof, 1-hexene, 1-heptene, and/or 1-octene; allyl alcohol, allylamine, allylbenzene, allylanisole, styrene, α-methylstyrene, 4-methylstyrene, and/or vinyl acetate.

It is preferable that the reaction of component C with components D and/or E takes place at a temperature of from 50 to 150° C.

A further process for preparation of mixtures as claimed in one or more of claims 1 to 3 comprises reacting component C, in a step 1, with a ketone to give 1-hydroxy-1-dialkylphosphinate, reacting this 1-hydroxy-1-dialkylphosphinate, in a step 2, in the presence of a free-radical initiator with component D, then, in a step 3, removing the ketone, and reacting the resultant reaction mixture, in a step 4, in the presence of a free-radical initiator with component E.

An alternative process for preparation of mixtures as claimed in one or more of claims 1 to 3 comprises reacting component C, in a step 1, with a ketone to give 1-hydroxy-1-dialkylphosphinate, reacting this 1-hydroxy-1-dialkylphosphinate, in a step 2, in the presence of a free-radical initiator with component D', then, in a step 3, removing the ketone, and reacting the resultant reaction mixture, in a step 4, in the presence of a free-radical initiator with component E, and then reacting the resultant monocarboxy-functionalized dialkylphosphinic acid thus obtained (where Y=H) with an alcohol YOH to give the monocarboxy-functionalized dialkylphosphinic ester A.

Another process for preparation of mixtures as claimed in one or more of claims 1 to 3 comprises reacting component C, in a step 1, with acetone to give 1-hydroxy-1-methylethylphosphinate, reacting this 1-hydroxy-1-methylethylphosphinate, in a step 2, in the presence of a free-radical initiator with component E, then, in a step 3, removing the acetone, and reacting the resultant reaction mixture, in a step 4, in the presence of a free-radical initiator with component D or D'.

It is preferable that, after the reaction with component D', the monocarboxy-functionalized dialkylphosphinic acid thus obtained (where Y=H) is reacted with an alcohol YOH to give the monocarboxy-functionalized dialkylphosphinic ester.

The invention also provides the use of mixtures as claimed in one or more of claims 1 to 3 as flame retardant or for preparation of flame retardants, of flame-retardant molding compositions, and/or of flame-retardant moldings, of flame-retardant films, of flame-retardant filaments, and of flame-retardant fibers.

In this use, the flame-retardant molding composition and, respectively, the moldings, films, filaments, and fibers comprise from 1 to 50% by weight of the mixtures as claimed in one or more of claims 1 to 3, from 1 to 99% by weight of polymer or a mixture of the same, from 0 to 60% by weight of additives, and from 0 to 60% by weight of filler, where the entirety of the components always amounts to 100% by weight.

In principle, mixtures are also suitable which comprise

A) from 98 to 100% by weight of monocarboxy-functionalized dialkylphosphinic ester of the formula (I)

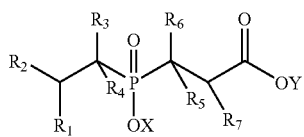

(I)

in which $R_1$, $R_2$, $R_3$, $R_4$, $R_5$, $R_6$, $R_7$ are identical or different and, independently of one another, are H, $C_1$-$C_{18}$-alkyl, $C_6$-$C_{18}$-aryl, $C_6$-$C_{18}$-aralkyl, $C_6$-$C_{18}$-alkylaryl, CN, CHO, OC(O)CH$_2$CN, CH(OH)C$_2$H$_5$, CH$_2$CH(OH)CH$_3$, 9-anthracene, 2-pyrrolidone, $(CH_2)_m$OH, $(CH_2)_m$NH$_2$, $(CH_2)_m$NCS, $(CH_2)_m$NC(S)NH$_2$, $(CH_2)_m$SH, $(CH_2)_m$S-2-thiazoline, $(CH_2)_m$SiMe$_3$, C(O)R$_8$, $(CH_2)_m$C(O)R$_8$, CH=CH—R$_8$, CH=CH—C(O)R$_8$, where $R_8$ is $C_1$-$C_{18}$-alkyl or $C_6$-$C_{18}$-aryl, and Y is $C_1$-$C_{18}$-alkyl, $C_6$-$C_{18}$-aryl, $C_6$-$C_{18}$-aralkyl, $C_6$-$C_{18}$-alkylaryl, $(CH_2)_k$OH, CH$_2$—CHOH—CH$_2$OH, $(CH_2)_k$O$(CH_2)_k$H, $(CH_2)_k$—CH(OH)—$(CH_2)_k$H, $(CH_2$—$CH_2$O$)_k$H, $(CH_2$—C[CH$_3$]HO$)_k$H, $(CH_2$—C[CH$_3$]HO$)_k$(CH$_2$—CH$_2$O$)_k$H, $(CH_2$—CH$_2$O$)_k$(CH$_2$—C[CH$_3$]HO)H, $(CH_2$—CH$_2$O$)_k$-alkyl, $(CH_2$—C[CH$_3$]HO$)_k$-alkyl, $(CH_2$—C[CH$_3$]HO$)_k$(CH$_2$—CH$_2$O$)_k$-alkyl, $(CH_2$—CH$_2$O$)_k$(CH$_2$—C[CH$_3$]HO)O-alkyl, $(CH_2)_k$—CH=CH$(CH_2)_k$H, $(CH_2)_k$NH$_2$, $(CH_2)_k$N[$(CH_2)_k$H]$_2$, where k is a whole number from 0 to 100, preferably from 2 to 10, and X is H, Li, Na, K or NH$_4$, or X is defined as for Y, and then X and Y are identical radicals or two different radicals of the above organic radicals, and m is a whole number from 0 to 10, preferably from 1 to 10, and B) from 0 to 2% by weight of halogens, where the entirety of the components always amounts to 100% by weight.

These mixtures preferably comprise from 99 to 100% by weight, in particular from 99.99 to 100% by weight, of monocarboxy-functionalized dialkylphosphinic ester of the formula (I) and from 0 to 1% by weight, in particular from 0 to 0.01% by weight, of halogens.

The groups $C_6$-$C_{18}$-aryl, $C_6$-$C_{18}$-aralkyl and $C_6$-$C_{18}$-alkylaryl can have substitution by SO$_3$X$_2$, —C(O)CH$_3$, OH, CH$_2$OH, CH$_3$SO$_3$X$_2$, PO$_3$X$_2$, NH$_2$, NO$_2$, OCH$_3$, SH, and/or OC(O)CH$_3$.

$R_1$, $R_2$, $R_3$, $R_4$, $R_5$, $R_6$, and $R_7$ can be identical or different and, independently of one another, are H, methyl, ethyl, n-propyl, isopropyl, n-butyl, isobutyl, tert-butyl and/or phenyl, in particular H and/or methyl.

X and Y can be identical or different and each can be methyl, ethyl, n-propyl, isopropyl, n-butyl, isobutyl, tert-butyl, phenyl, ethylene glycol, propyl glycol, butyl glycol, pentyl glycol, hexyl glycol, allyl, and/or glycerol. H is preferred for X.

It is preferable that the mixtures comprise A) from 99.9995 to 100% by weight of methyl 3-(ethylhydroxyphosphinyl) propionate, 2-hydroxyethyl 3-(ethylhydroxyphosphinyl)propionate, 2,3-dihydroxypropyl 3-(ethylhydroxyphosphinyl) propionate, allyl 3-(ethylhydroxyphosphinyl)-2-methylpropionate, 4-hydroxybutyl 3-(ethylhydroxyphosphinyl)-2-methylpropionate, 6-hydroxyhexyl 3-(ethylhydroxyphosphinyl)-propionate, 2-hydroxyethyl 3-(ethyl-n-butoxyphosphinyl)isobutyrate, butyl 3-(ethyl-n-butoxyphosphinyl)propionate, methyl 3-(ethylmethoxyphosphinyl)propionate, butyl 3-(propylhydroxyphosphinyl)propionate, 2-hydroxyethyl 3-(propylhydroxyphosphinyl)propionate, 2-hydroxypropyl 3-(propylhydroxyphosphinyl)propionate, 2-hydroxypropyl 3-(propylhydroxyphosphinyl)-2-methylpropionate, methyl 3-(propylhydroxyphosphinyl)propionate, 2-hydroxyethyl 3-(butylhydroxyphosphinyl)propionate, 3-hydroxypropyl 3-(hexylhydroxyphosphinyl)propionate, 2-hydroxyethyl 3-(ethylhydroxyphosphinyl)-2-methylbutyrate, 2-hydroxyethyl 3-(propylhydroxyphosphinyl)-2-methylbutyrate, 2-hydroxypropyl 3-(ethylhydroxyphosphinyl)-2-methylbutyrate, 2-hydroxypropyl 3-(propylhydroxyphosphinyl)-2-methylbutyrate, 2,3-dihydroxypropyl 3-(propylhydroxyphosphinyl)

propionate, and/or methyl 3-(ethylmethoxyphosphinyl)-2-methylbutyrate, and B) from 0 to 0.0005% by weight of chlorine.

The invention also provides a process for preparation of the abovementioned mixtures, which comprises reacting hypophosphorous acid or its salts (component C) in the presence of a free-radical initiator with an α,β-unsaturated carboxylic acid derivative (component D) or with an α,β-unsaturated carboxylic acid (component D') and with an olefin (component E).

If Z is $C_{6-18}$-aryl, it is preferable that this group has substitution by $SO_3X_2$, —$C(O)CH_3$, OH, $CH_2OH$, $CH_3SO_3X_2$, $PO_3X_2$, $NH_2$, $NO_2$, $OCH_3$, SH and/or $OC(O)CH_3$.

It is preferable that Y is, for example, methyl, ethyl, n-propyl, isopropyl, allyl, n-butyl, 2-butyl, tert-butyl, isobutyl, n-hexyl and/or phenyl; 2-hydroxyethyl, 2,3-dihydroxypropyl, 2-hydroxypropyl, 3-hydroxypropyl, 4-hydroxybutyl, 3-hydroxybutyl, 2-hydroxybutyl and/or 6-hydroxyhexyl; 2-methoxyethyl, 2-ethoxyethyl, 2-butoxyethyl, 2-dodecyloxyethyl, methyl diglycol, ethyl diglycol, and/or polyglycol.

It is preferable that, in a first step of the process, component C is reacted in the presence of a free-radical initiator with component D or D', and in a second step of the process the resultant reaction solution is reacted likewise in the presence of a free-radical initiator with component E.

It is preferable that, in a first step of the process, component C is reacted in the presence of a free-radical initiator with component E and, in a second step of the process, the resultant reaction solution is reacted likewise in the presence of a free-radical initiator with component D or D'.

It is preferable to use the following molar ratios of components C, D, (D'), and E:

$$pC + \sum_{k=1}^{n-1} x_k D + \sum_{k=1}^{n-1} y_k E + (\alpha - x_n)D + (\alpha - y_n)E = A$$

where C is hypophosphorous acid or its salts of the formula II, D is the α,β-unsaturated carboxylic acid derivative of the formula III or the α,β-unsaturated carboxylic acid (D') of the formula IV, E is the olefin of the formula V, and A is the monocarboxy-functionalized dialkylphosphinic ester of the formula I, and moreover:

$$\sum_{k=1}^{n} x_k = \alpha \text{ and } \sum_{k=1}^{n} y_k = \alpha,$$

where α=from 1 to 3; $0.01 \leq x_k$, and $y_k \leq \alpha$; p=from 0.5 to 3, and n=from 1 to 100.

It is also preferable that the conduct of the process is such that, in a first step 1, component C is reacted in the presence of a free-radical initiator with a portion $x_k$ D of component D or with a portion $x_n$ D' of component D', the resultant reaction solution is reacted, in a step 2, in the presence of a free-radical initiator with the entire amount of component E, and the resultant reaction solution is reacted, in a step 3, in the presence of a free-radical initiator with the remaining portion $(\alpha-x_n)$ D of component D or with the remaining portion $(\alpha-x_n)$ D' of component D'.

It is preferable that, in a first step 1, component C is reacted in the presence of a free-radical initiator with a portion $y_k$ E of component E, the resultant reaction solution is reacted, in a step 2, in the presence of a free-radical initiator with the entire amount of component D or D', and the resultant reaction solution is reacted, in a step 3, in the presence of a free-radical initiator with the remaining portion $(\alpha-y_n)$ E of component E.

It is preferable that, in a step 1, component C is reacted in the presence of a free-radical initiator with a portion $x_k$ D of component D or with a portion x'n' D' of component D', and the resultant reaction solution is reacted, in a step 2, in the presence of a free-radical initiator with a portion $y_k$ E of component E, where the number of alternations of steps 1 and 2 is sufficient to consume the respective portions.

It is preferable that, in a step 1, component C is reacted in the presence of a free-radical initiator with a portion $y_k$ E of component E, and the resultant reaction solution is reacted, in a step 2, in the presence of a free-radical initiator with a portion $x_k$ D of component D or with a portion $x_n$ D' of component D', where the number of alternations of steps 1 and 2 is sufficient to consume the respective portions.

It is preferable that, in a step 1, component C is reacted in the presence of a free-radical initiator with component E to give an alkylphosphonous acid and, in step 2, the resultant reaction solution is esterified with an alcohol M-OH and phosphonous ester produced here is removed by distillation and then, in a step 3, is reacted in the presence of a free-radical initiator or of a basic initiator with component D to give the monocarboxy-functionalized dialkylphosphinic ester.

The initiator is preferably peroxide-forming compounds and/or peroxo compounds, e.g. hydrogen peroxide, sodium peroxide, lithium peroxide, potassium persulfate, sodium persulfate, ammonium persulfate, sodium peroxodisulfate, potassium peroxoborate, peracetic acid, benzoyl peroxide, di-tert-butyl peroxide and/or peroxodisulfuric acid, and/or is azo compounds, e.g. azodiisobutyronitrile, 2,2'-azobis(2-amidinopropane) dihydrochloride, and/or 2,2'-azobis(N,N'-dimethyleneisobutyramidine) dihydrochloride.

The α,β-unsaturated carboxylic acids are also preferably furan-2-carboxylic acid and/or thiophene-2-carboxylic acid.

It is preferable that the amounts used of the free-radical initiator are from 0.001 to 10 mol %, based on the phosphorus-containing compound.

It is preferable that the rate of feed of the free-radical initiator is from 0.01 to 10 mol % of initiator per hour, based on the phosphorus-containing compound.

It is preferable that the ratio of olefin to hypophosphite and/or hypophosphorous acid (on a molar basis) is from 1:3 to 3:0.5, in particular from 1.5:3 to 2.5:1.

It is preferable that the reaction with the olefin component E takes place at a pressure of the olefin used of from 1 to 100 bar, in particular from 2 to 50 bar.

It is preferable that the reaction of component C with components D and/or E takes place at a temperature of from 0 to 250° C., in particular at from 20 to 200° C. and very particularly preferably at from 50 to 150° C.

It is preferable that the flame retardant comprises from 0.1 to 90% by weight of the mixtures as claimed in one or more of claims 1 to 11 and from 0.1 to 50% by weight of further additives, where the entirety of the components always amounts to 100% by weight.

It is particularly preferable that the flame retardant comprises from 10 to 80% by weight of the mixtures as claimed in one or more of claims 1 to 11 and from 10 to 40% by weight of further additives, where the entirety of the components always amounts to 100% by weight.

It is particularly preferable that the flame-retardant molding composition comprises from 5 to 30% by weight of the mixtures as claimed in one or more of claims 1 to 11, from 5 to 9% by weight of polymer or a mixture of the same, from 5 to 40% by weight of additives, and from 5 to 40% by weight of filler, where the entirety of the components always amounts to 100% by weight.

It is particularly preferable that the moldings, films, filaments, and fibers comprise from 5 to 30% by weight of the mixtures as claimed in one or more of claims 1 to 11, from 5 to 90% by weight of polymer or a mixture of the same, from 5 to 40% by weight of additives, and from 5 to 40% by weight of filler, where the entirety of the components always amounts to 100% by weight.

The additives are preferably antioxidants, antistatic agents, blowing agents, further flame retardants, heat stabilizers, impact modifiers, processing auxiliaries, lubricants, light stabilizers, antidrip agents, compatibilizers, reinforcing materials, nucleating agents, additives for laser marking, hydrolysis stabilizers, chain extenders, color pigments, and/or plasticizers.

X can be defined as for Y, and X is preferably H when Y is one of the abovementioned organic radicals. However, X can also be an organic radical identical with Y, or X and Y can be different organic radicals.

The inventive process has considerable advantages over the prior art, since it entirely avoids phosphonous dihalides and other halogen-containing compounds. With this, the inventive monocarboxy-functionalized dialkylphosphinic esters in the form of their mixtures, are also much less corrosive than the monocarboxy-functionalized dialkylphosphinic esters obtainable hitherto. The lower corrosivity is advantageous not only for handling during the preparation process but also during use as flame retardant.

The inventive preparation processes give access to monocarboxy-functionalized dialkylphosphinic salts in completely halogen-free form, the freedom from halogen here being at a level not accessible in the prior art known hitherto.

The inventive processes have the advantage of starting from halogen-free starting materials, and the final products are therefore likewise completely halogen-free. The content of halogens—if indeed such content is present—is below the detectable limit. In contrast, all of the processes known hitherto from the prior art lead to substantially higher halogen content in the respective final product.

As described above, the process of the invention reacts component C in the presence of a free-radical initiator with component D or D' and E in a solvent, components D and, respectively D' and E being fed separately (in series or in sequence) rather than simultaneously. If component D (carboxylic ester) is used prior to or after addition of component E, the inventive monocarboxy-functionalized dialkylphosphinic ester is obtained directly. If component D' (free carboxylic acid) is used prior to or after addition of component E, the monocarboxy-functionalized dialkylphosphinic acid (where Y=H) is first obtained, and is then reacted in the following step with an alcohol YOH to give the inventive monocarboxy-functionalized dialkylphosphinic ester A.

Surprisingly, the monocarboxy-functionalized dialkylphosphinic acid can be obtained in good yields via iterative reaction of $\alpha,\beta$-unsaturated carboxylic acids or $\alpha,\beta$-unsaturated carboxylic esters and olefins with derivatives of hypophosphorous acid without isolation of the respective monoalkylphosphinic acid derivative. Reaction with an $\alpha,\beta$-unsaturated carboxylic acid D' always also requires esterification with an alcohol YOH, in order to obtain the free monocarboxy-functionalized dialkylphosphinic acid.

Esterification of the phosphonous acid to give the corresponding monoester (step b) can, for example, be achieved via reaction with relatively high-boiling-point alcohols, while using azeotropic distillation to remove the water formed.

It is preferable that, in step b), the ester of the alkylphosphonous acid is purified by distillation.

It is preferable that the basic initiators are alkali metal alcoholates and/or alkaline earth metal alcoholates. It is particularly preferable to use sodium methanolate, sodium ethanolate, or sodium butanolate.

The ratio of $\alpha,\beta$-unsaturated carboxylic acid and olefins to hypophosphite and/or hypophosphorous acid (on a molar basis) is preferably given by: $0.01 \leq x_k$ and $y_k \leq \alpha$, $\alpha=1-3$, $p=0.5-3.0$, and $n=1-100$, particularly preferably $0.05 \leq x_k$ and $y_k \leq \alpha$, $\alpha=1-1.5$, $p=0.8-1.2$, $n=2-20$.

It is preferable that inorganic solvents, particularly water, organic solvents, or any desired mixture of the same are used.

The pH is adjusted to from 0 to 14 in the case of aqueous solvent, preferably from 2 to 9.

It is preferable that the pH is adjusted using mineral acids, acidic salts, carboxylic acids, alkalis and/or electrolytes, e.g. sodium bisulfate, sodium bisulfite, and/or potassium bisulfite.

It is preferable that the carboxylic acids are formic acid, acetic acid, propionic acid, butyric acid, and/or relatively-long-chain carboxylic acids, and/or their dimers, oligomers, and/or polymers.

It is preferable that the salt of hypophosphorous acid is a salt whose cation is an element of the $1^{st}$ main group and/or whose cation is based on an organically substituted element of the $5^{th}$ main group. It is particularly preferable that it is an ammonium salt or an alkali metal salt, in particular the sodium salt.

It is preferable that the hypophosphorous acid is prepared in situ from salts of hypophosphorous acid and from at least one mineral acid, the ratio of additive acid to hypophosphite (based on equivalents) being from 0:1 to 2:1.

Particularly preferred free-radical initiators are peroxo compounds, such as peroxomonosulfuric acid, potassium persulfate (potassium peroxomonosulfate), caroate(TM), oxones(TM), peroxodisulfuric acid, potassium persulfate (potassium peroxodisulfate), sodium persulfate (sodium peroxodisulfate), ammonium persulfate (ammonium peroxodisulfate).

Particular preference is given to compounds which can form peroxides in the solvent system, e.g. sodium peroxide, sodium peroxide diperoxohydrate, sodium peroxide diperoxohydrate hydrate, sodium peroxide dihydrate, sodium peroxide octahydrate, lithium peroxide, lithium peroxide monoperoxohydrate trihydrate, calcium peroxide, strontium peroxide, barium peroxide, magnesium peroxide, zinc peroxide, potassium hyperoxide, potassium peroxide diperoxohydrate, sodium peroxoborate tetrahydrate, sodium peroxoborate trihydrate, sodium peroxoborate monohydrate, anhydrous sodium peroxoborate, potassium peroxoborate peroxohydrate, magnesium peroxoborate, calcium peroxoborate, barium peroxoborate, strontium peroxoborate, potassium peroxoborate, peroxomonophosphoric acid, peroxodiphosphoric acid, potassium peroxodiphosphate, ammonium peroxodiphosphate, potassium ammonium peroxodiphosphates (double salt), sodium carbonate peroxohydrate, urea peroxohydrate, ammonium oxalate peroxide, barium peroxide peroxohydrate, calcium hydrogen peroxides, calcium peroxide peroxohydrate, ammonium triphosphate diperoxophosphate hydrate, potassium fluoride peroxohydrate, potassium fluoride triperoxohydrate, potassium fluoride diperoxohydrate, sodium pyrophosphate diperoxohydrate, sodium pyrophosphate diperoxohydrate octahydrate, potassium acetate peroxohydrate, sodium phosphate peroxohydrate, sodium silicate peroxohydrate.

Particular preference is given to hydrogen peroxide, performic acid, peracetic acid, benzoyl peroxide, di-tert-butyl peroxide, dicumyl peroxide, 2,4-dichlorobenzoyl peroxide, decanoyl peroxide, lauroyl peroxide, cumene hydroperoxide, pinene hydroperoxide, p-menthane hydroperoxide, tert-butyl hydroperoxide, acetylacetone peroxide, methyl ethyl ketone peroxide, succinic acid peroxide, dicetyl peroxydicarbonate, tert-butyl peroxyacetate, tert-butyl peroxymaleate, tert-butyl peroxybenzoate, acetylcyclohexylsulfonyl peroxide.

It is preferable that water-soluble azo compounds are used as free-radical initiator.

Particular preference is given to azo initiators such as ®VAZO 52, ®VAZO 64 (AIBN), ®VAZO 67, ®VAZO 88, ®VAZO 68 from Dupont-Biesteritz, V-70 2,2'-azobis(4-methoxy-2,4-dimethylvaleronitrile), V-65 2,2'-azobis(2,4-dimethylvaleronitrile), V-601 dimethyl 2,2'-azobis(2-methylpropionate), V-59 2,2'-azobis(2-methylbutyronitrile), V-40, VF-096 1,1'-azobis(cyclohexane-1-carbonitrile), V-30 1-[(cyano-1-methylethyl)azo]formamide, VAm-110 2,2'-azobis(N-butyl-2-methylpropionamide), VAm-111 2,2'-azobis(N-cyclohexyl-2-methylpropionamide), VA-046B 2,2'-azobis[2-(2-imidazolin-2-yl)propane disulfate dihydrate, VA-057 2,2'-azobis[N-(2-carboxyethyl)-2-methylpropionamidine]tetrahydrate, VA-061 2,2'-azobis[2-(2-imidazolin-2-yl)propane], VA-080 2,2'-azobis{2-methyl-N-[1,1-bis(hydroxymethyl)-2-hydroxyethyl]propionamide}, VA-085 2,2'-azobis{2-methyl-N-[2-(1-hydroxybutyl)]propionamide}, VA-086 2,2'-azobis[2-methyl-N-(2-hydroxyethyl)propionamide] from Wako Chemicals.

Further preference is given to azo initiators such as 2-tert-butylazo-2-cyanopropane, dimethyl azodiisobutyrate, azodiisobutyronitrile, 2-tert-butylazo-1-cyanocyclohexane, 1-tert-amylazo-1-cyanocyclohexane. Preference is moreover given to alkyl perketals such as 2,2-bis(tert-butylperoxy)butane, ethyl-3,3-bis(tert-butylperoxy)butyrate, 1,1-di-(tert-butylperoxy)cyclohexane.

It is preferable that the amounts used of the free-radical initiator are from 0.05 to 5 mol %, based on the respective unsaturated organic component D and/or E. The free-radical initiator is preferably used in the solvent mentioned.

It is preferable that the α,β-unsaturated carboxylic esters (component D) used comprise methyl acrylate, ethyl acrylate, butyl acrylate, tert-butyl acrylate, isobutyl acrylate, 2-ethylhexyl acrylate, 2-hydroxyethyl acrylate, 2-hydroxypropyl acrylate, 2-methoxyethyl acrylate, stearyl acrylate, behenyl acrylate, methyl methacrylate, ethyl methacrylate, butyl methacrylate, dodecyl methacrylate, isobornyl methacrylate, 2-hydroxyethyl methacrylate, 2-hydroxypropyl methacrylate, lauryl methacrylate, ethyl crotonate, ethyl 2-cyano-3-ethoxyacrylate, allyl methacrylate, 2-dimethylaminoethyl methacrylate, 2-ethoxyethyl methacrylate, 2-ethoxyethyl acrylate, ethyl 3-dimethylaminoacrylate, 1,6-hexanediol diacrylate, dipropylene glycol acrylate, tripropylene glycol acrylate, or ethyl diglycol acrylate.

It is preferable that the α,β-unsaturated carboxylic acid (component D') used comprises acrylic acid, methacrylic acid, crotonic acid, tiglic acid (trans-2,3-dimethylacrylic acid), (trans-)2-pentenoic acid, furan-2-carboxylic acid, or thiophene-2-carboxylic acid.

The olefins (component E) used preferably comprise linear or branched olefins having a carbon chain length of $C_1$-$C_{18}$. Particular preference is given to ethylene, propylene, n-butene and/or isobutene, or any desired mixture thereof, 1-hexene, 1-heptene, and 1-octene.

Cyclic olefins are also suitable, particularly cyclopentene, cyclohexene, cyclohexenols, cyclohexenones, cycloheptene, cyclooctene, cyclooctenols, or cyclooctenones.

Functionalized olefins are also suitable, preferably allyl isothiocyanate, allyl methacrylate, 2-allylphenol, N-allylthiourea, 2-(allylthio)-2-thiazoline, allyltrimethylsilane, allyl acetate, allyl acetoacetate, allyl alcohol, allylamine, allylbenzene, allyl cyanide, allyl cyanoacetate, allylanisole, trans-2-pentenal, cis-2-pentenonitrile, 1-penten-3-ol, 4-penten-1-ol, 4-penten-2-ol, trans-2-hexenal, trans-2-hexen-1-ol, cis-3-hexen-1-ol, 5-hexen-1-ol, styrene, α-methylstyrene, 4-methylstyrene, vinyl acetate, 9-vinyl anthracene, 2-vinylpyridine, 4-vinylpyridine, and 1-vinyl-2-pyrrolidone.

Alcohols YOH are used for esterification of the monocarboxy-functionalized dialkylphosphinic acid. Preference is given to linear or branched, mono- or polyhydric organic alcohols or polyols. Preference is given to primary, secondary, or tertiary alcohols whose carbon chain length is $C_{1-18}$. Particular preference is given to the saturated, monohydric alcohols methanol, ethanol, propanol, isopropanol, n-butanol, 2-butanol, tert-butanol, amyl alcohol, and/or hexanol.

It is preferable that the polyhydric, saturated alcohols used comprise ethylene glycol, propylene 1,2-glycol, propylene 1,3-glycol, 1,4-butanediol, 2,2-dimethylpropane-1,3-diol, neopentyl glycol, 1,6-hexanediol, cyclohexane-1,4-dimethanol, glycerol, trishydroxymethylethane, trishydroxymethylpropane, pentaerythritol, sorbitol, mannitol, α-naphthol, polyethylene glycols, polypropylene glykols, and EO-PO block polymers. Particular preference is given to ethylene glycol, propylene 1,2-glycol, propylene 1,3-glycol, 1,4-butanediol, and 1,6-hexanediol.

Mono- or polyhydric, unsaturated alcohols whose carbon chain length is $C_{1-18}$ are also suitable. Particular preference is then given to n-but-1-en-2-ol, 1,4-butenediol, and allyl alcohol.

Reaction products of monohydric alcohols with one or more molecules of alkylene oxide, particularly preferably ethylene oxide and propylene 1,2-oxide, are also suitable. Preference is given to 2-methoxyethanol, 2-ethoxyethanol, 2-n-butoxyethanol, 2-(2'-ethylhexyloxy)ethanol, 2-n-dodecyloxyethanol, methyl diglycol, ethyl diglycol, and isopropyl diglycol, fatty alcohol polyglycol ethers, and aryl polyglycol ethers.

Preference is also given to reaction products of polyhydric alcohols with one or more molecules of alkylene oxide, in particular diglycol and triglycol, and also adducts of from 1 to 6 molecules of ethylene oxide or propylene oxide onto glycerol, trishydroxymethylpropane or pentaerythritol.

In another embodiment, preference is given to use of reaction products of water with one or more molecules of alkylene oxide. Preference is given to polyethylene glycols and polypropylene 1,2-glycols of various molecular sizes whose average molar mass is from 100 to 1000 g/mol, particularly preferably from 150 to 350 g/mol.

Preference is also given to reaction products of ethylene oxide with polypropylene 1,2-glycols or to fatty alcohol propylene glycols; likewise reaction products of propylene 1,2-oxide with polyethylene glycols or with fatty alcohol ethoxylates. Preference is given to those reaction products whose average molar mass is from 100 to 1000 g/mol, particularly preferably from 150 to 450 g/mol.

It is also possible to use reaction products of alkylene oxides with ammonia, or with primary or secondary amines, with hydrogen sulfide, or with mercaptans, oxy acids of phosphorus, $C_2$-$C_6$ carboxylic acids and $C_2$-$C_6$ dicarboxylic acids. Particularly preferred reaction products of ethylene oxide with nitrogen compounds are triethanolamine, methyldiethanolamine, n-butyldieithanolamine, n-dodecyldiethanolamine, dimethylethanolamine, n-butylmethylethanolamine, di-n-butylethanolamine, n-dodecylmethylethanolamine, tetrahydroxyethylethylenediamine, or pentahydroxyethyldiethylenetriamine.

It is preferable that during the reaction with the α,β-unsaturated carboxylic acid derivative (component D or D') the atmosphere is composed of from 50 to 99.9% by weight, preferably from 70 to 95% by weight, of constituents of the solvent and α,β-unsaturated carboxylic acid.

It is preferable that during the reaction with the olefin (component E) the atmosphere is composed of from 50 to 99.9% by weight, preferably from 70 to 95% by weight, of constituents of the solvent and olefin.

The atmosphere preferably comprises gaseous components which do not participate in the reaction.

The gaseous components are preferably oxygen, nitrogen, carbon dioxide, noble gases, hydrogen, and/or alkanes.

It is preferable that the reaction takes place during addition of the α,β-unsaturated carboxylic acid derivative (component D or D') at a pressure of from 1 to 20 bar.

It is preferable that during the reaction of component C with components D and, respectively, D' or E the reaction solution is subject to an intensity of mixing corresponding to a rotational Reynolds number of from 1 to 1 000 000, preferably from 100 to 100 000.

It is preferable that olefin, α,β-unsaturated carboxylic acid derivative, free-radical initiator, solvent, and hypophosphorous acid, and/or salts thereof are intimately mixed with energy input of from 0.083 to 10 kW/m$^3$, preferably from 0.33 to 1.65 kW/m$^3$.

Preferred apparatuses are stirred tanks, stirred-tank cascades, flow tubes, bubble columns, and scrubbers.

It is preferable that gaseous olefin components are introduced via nozzles (e.g. venturi nozzles), gassing stirrers, turbine stirrers, disk stirrers.

The invention also provides flame retardants which comprise the inventive low-halogen-content monocarboxy-functionalized dialkylphosphinic esters.

Preference is given to a flame retardant comprising from 0.1 to 90% by weight of the low-halogen-content monocarboxy-functionalized dialkylphosphinic esters and from 0.1 to 50% by weight of further additives, particularly preferably diols.

Preference is given to a flame retardant comprising from 10 to 80% by weight of the low-halogen-content monocarboxy-functionalized dialkylphosphinic esters and from 10 to 40% by weight of further additives, particularly preferably diols.

Preferred additives for the inventive stabilized flame retardants are antioxidants such as aromatic amines, sterically hindered phenols (butylated hydroxytoluene (BHT)), thiobisphenol, relatively high-molecular-weight polyphenols, tetrakis(methylene[2,5-di-tert-butyl-4-hydroxyhydrocinnamate])methane (®Irganox 1010), octadecyl 3,5-di-tert-butyl-4-hydroxyhydrocinnamate (®Irganox 1076), organophosphites (tris(nonylphenyl)phosphite (TNPP)), thioesters (distearyl 3,3'-thiodipropionates, ditridecyl 3,3'-thiodipropionate, dilauryl 3,3'-thiodipropionate), metal deactivators (®Irganox 1024), vitamin E (alpha-tocopherol), lactone, hydroxylamine.

Other preferred additives are antistatic agents, such as fatty acid esters (glycerol, polyethylene glycol esters, sorbitol esters), quaternary ammonium compounds, ethoxylated amines, alkylsulfonates.

Other preferred additives are blowing agents such as azodicarbonamide, p,p-oxybis(benzenesulfonyl hydrazide) (OBSH), 5-phenyltetrazole (5PT), p-toluenesulfonylsemicarbazide (TSSC), trihydrazinotriazine (THT).

Other preferred additives are alumina trihydrate, antimony oxide, brominated aromatic or cycloaliphatic hydrocarbons, phenols, ethers, chloroparaffin, hexachlorocyclopentadiene adducts (®Dechloran Plus, Occidental Chemical Co), red phosphorus, melamine derivatives, melamine cyanurates, ammonium polyphosphates, magnesium hydroxide.

Other preferred additives are heat stabilizers such as lead stabilizers, (dibasic lead phthalate, dibasic lead stearate, lead silicate, monobasic and tribasic lead sulfate, dibasic lead carbonate, dibasic lead phosphite), mixed metal salts (barium cadmium salts of, and barium zinc salts and calcium zinc salts of, 2-ethylhexylcarboxylic acid), stearic acid, ricinoleic acid, and/or lauric acid and, respectively, substituted phenols, organotin stabilizers (mono- and dialkyltin mercaptides, (thioglycolates), dialkyltin carboxylates (maleates, laurates, tin esters)), secondary heat stabilizers (alkyl/aryl organophosphites, epoxy compounds of unsaturated fatty acids, and esters of fatty acids).

Other preferred additives are impact modifiers/processing auxiliaries such as acrylates, acrylonitrile-butadiene-styrene (ABS), chlorinated polyethylene (CPE), ethylene-propylene terpolymer (EPT), ethylenevinyl acetate (EVA), methacrylate-butadiene-styrene (MBS).

Other preferred additives are lubricants such as fatty acid amides (fatty acid monoamides, fatty acid bisamides, oleamides, erucamides, ethylenebisstearamide (EBSA), ethylenebisoleamide (EBOA)), fatty acid/esters of fatty acids ($C_{16}$-$C_{18}$ (palmitic acid, stearic acid, oleic acid)), fatty acid alcohols (cetyl alcohol, stearyl alcohol), waxes (paraffin waxes, polyethylene waxes), metal stearates (calcium stearate, zinc stearate, magnesium stearate, barium stearate, aluminum stearate, cadmium stearate, lead stearate).

Other preferred additives are light stabilizers such as UV absorbers (alkyl-substituted hydroxybenzophenones e.g. 2-hydroxy-4-alkoxybenzophenones, alkyl-substituted hydroxybenzothiazoles e.g. 2-hydroxy-3,5-dialkylbenzotriazoles), UV quenchers (nickel diethyldithiocarbamate and zinc diethyldithiocarbamate, n-butylaminenickel 2,2'-thiobis (4-tert-octylphenolate), nickel bis(monoethyl 3,5-di-tert-butyl-4-hydroxybenzyl)phosphonate), free-radical inhibitors (bis(2,2',6,6'-tetramethyl-4-piperidyl)sebacate (HALS)), agents that decompose hydroperoxide (dithiophosphates).

Further preference is given to antidrip agents, compatibilizers, fillers, reinforcing materials, nucleating agents, additives for laser marking, hydrolysis stabilizers, chain extenders, color pigments, and plasticizers.

The invention in particular provides the use of the inventive monocarboxy-functionalized dialkylphosphinic esters as flame retardant for thermoplastic polymers such as polyesters, polystyrene, or polyamide, and for thermoset polymers such as unsaturated polyester resins, epoxy resins, polyurethanes, or acrylates.

The invention in particular provides the use of the inventive monocarboxy-functionalized dialkylphosphinic esters as intermediate for preparation of flame retardants for thermoplastic polymers, such as polyesters, polystyrene, or polyamide, and for thermoset polymers, such as unsaturated polyester resins, epoxy resins, polyurethanes, or acrylates.

The invention also provides the use of the inventive monocarboxy-functionalized dialkylphosphinic esters as intermediate for production of flame retardants, or as flame retardants for thermoplastic polymers, such as polyesters, polystyrene, or polyamide, and for thermoset polymers, such as unsaturated polyester resins, epoxy resins, polyurethanes, or acrylates.

Suitable polyesters derive from dicarboxylic acids and from diols and/or from hydroxycarboxylic acids or from the corresponding lactones.

It is preferable that the dicarboxylic acid components or their esters used comprise terephthalic acid, isophthalic acid, 5-sulfoisophthalic acid, 5-sulfopropoxyisophthalic acid, naphthalene-2,6-dicarboxylic acid, diphenyl-p,p'-dicarboxylic acid, diphenoxyalkanedicarboxylic acids, trans-hexahydroterephthalic acid, adipic acid, sebacic acid, or 1,2-cyclobutanedicarboxylic acid. It is particularly preferable to use terephthalic acid.

It is particularly preferable to use terephthalic acid as main component.

It is preferable that the entirety of the dicarboxylic acid co-components amounts to at most 10 mol % of the entire dicarboxylic acid component.

For polyester preparation, it is preferable that the diol component is used in pure form or as co-component to another diol.

For polyester preparation, it is preferable that the diol components used comprise ethylene glycol, propane-1,3-diol, butane-1,3-diol, and the higher homologs of butane-1,3-diols, 2,2-dimethylpropane-1,3-diol, or 1,4-cyclohexanedimethanol, particularly preferably ethylene glycol. It is preferable here for polyester preparation that the entirety of the diol co-components amounts to at most 10 mol % of the entire diol component.

For polyester preparation it is preferable that ethylene glycol is used as main component.

Suitable polyesters are polyethylene terephthalate, polybutylene terephthalate (®Celanex 2500, ®Celanex 2002, Celanese; ®Ultradur, BASF), poly-1,4-dimethylolcyclohexane terephthalate, polyhydroxybenzoates, and also block polyetheresters which derive from polyethers having hydroxy end groups; and polyesters modified with polycarbonates or modified with MBS.

Synthetic linear polyesters with permanent flame retarding are composed of dicarboxylic acid components, of diol components of the inventive low-halogen-content monocarboxy-functionalized dialkylphosphinic esters or of the monocarboxy-functionalized dialkylphosphinic esters prepared by the inventive process, as phosphorus-containing chain members. The phosphorus-containing chain members make up from 2 to 20% of the dicarboxylic acid content of the polyester. The resultant phosphorus content in the polyester is preferably from 0.1 to 5%, particularly preferably from 0.5 to 3%.

For preparation of the molding composition it is preferable to carry out direct esterification starting from the free dicarboxylic acid and diols, with subsequent polycondensation.

It is preferable to begin by carrying out transesterification starting from dicarboxylic esters, in particular dimethyl esters, and then to carry out polycondensation using the catalysts conventionally used for this purpose.

During preparation of the polyester, the following can preferably also be added, beside the familiar catalysts: conventional additives (crosslinking agents, matting agents and stabilizers, nucleating agents, dyes and fillers, etc.).

It is preferable that the inventive mixtures are added prior to, during, or shortly prior to the end of, the polycondensation reaction.

It is preferable that the esterification takes place at temperatures of from 100 to 300° C., particularly from 150 to 250° C.

It is preferable that the polycondensation reaction is carried out at pressures of from 0.1 to 1.5 mbar and at temperatures of from 150 to 450° C., particularly from 200 to 300° C.

It is preferable that the flame-retardant polyester molding compositions prepared according to the invention are used in polyester moldings.

Preferred polyester moldings are filaments, fibers, foils, and moldings, comprising mainly terephthalic acid as dicarboxylic acid component and mainly ethylene glycol as diol component.

Preferred process for production of filaments and fibers is spinning, drawing, and post-treatment. Preferred processes for production of foils are extrusion, pressing, and injection molding.

It is preferable that the phosphorus content in filaments and fibers produced from flame-retardant polyester is from 0.1 to 18%, preferably from 0.5 to 15%.

It is preferable that the phosphorus content in foils produced from flame-retardant polyester is from 0.2 to 15%, preferably from 0.9 to 12%.

The inventively flame-retardant polyester filaments can preferably be used in single-component filaments or else as one component in bicomponent filaments together with other polymers.

Suitable polystyrenes are polystyrene, poly(p-methylstyrene), and/or poly(alpha-methylstyrene).

It is preferable that the suitable polystyrenes are copolymers of styrene or alpha-methylstyrene with dienes or with acrylic derivatives, e.g. styrene-butadiene, styrene-acrylonitrile, styrene-alkyl methacrylate, styrene-butadiene-alkyl acrylate, styrene-butadiene-alkyl methacrylate, styrene-maleic anhydride, styrene-acrylonitrile-methyl acrylate; or a mixture of high impact resistance composed of styrene copolymers and of another polymer, e.g. of a polyacrylate, of a diene polymer, or of an ethylene-propylene-diene terpolymer; or else block copolymers of styrene, e.g. styrene-butadiene-styrene, styrene-isoprene-styrene, styrene-ethylene/butylene-styrene, or styrene-ethylene/propylene-styrene.

Other preferable suitable polystyrenes are graft copolymers of styrene or alpha-methylstyrene, e.g. styrene on polybutadiene, styrene on polybutadiene-styrene copolymers or on polybutadiene-acrylonitrile copolymers, styrene and acrylonitrile (and, respectively, methacrylonitrile) on polybutadiene; styrene, acrylonitrile, and methyl methacrylate on polybutadiene; styrene and maleic anhydride on polybutadiene; styrene, acrylonitrile, and maleic anhydride or maleimide on polybutadiene; styrene and maleimide on polybutadiene, styrene and alkyl acrylates, respectively, alkyl methacrylates on polybutadiene, styrene and acrylonitrile on ethylene-propylene-diene terpolymers, styrene and acrylonitrile on polyalkyl acrylates or on polyalkyl methacrylates, styrene and acrylonitrile on acrylate-butadiene copolymers, or else a mixture of these, e.g. those known as ABS polymers, MBS polymers, ASA polymers, or AES polymers.

It is preferable that the polymers are polyamides and copolyamides which derive from diamines and from dicarboxylic acids, and/or from aminocarboxylic acids or from the corresponding lactams, examples being nylon-2,12, nylon-4 (poly-4-aminobutyric acid, ®Nylon 4, DuPont), nylon-4,6 (poly(tetramethyleneadipamide), poly(tetramethyleneadipic diamide), ®Nylon 4/6, DuPont), nylon-6 (polycaprolactam, poly-6-aminohexanoic acid, ®Nylon 6, DuPont, ®Akulon K122, DSM; ®Zytel 7301, DuPont; ®Durethan B 29, Bayer), nylon-6,6 (poly(N,N'-hexamethyleneadipic diamide), ®Nylon 6/6, DuPont, ®Zytel 101, DuPont; ®Durethan A30, ®Durethan AKV, ®Durethan AM, Bayer; ®Ultramid A3, BASF), nylon-6,9 (poly(hexamethylenenonane diamide), ®Nylon 6/9, DuPont), nylon-6,10 (poly(hexamethylenesebacamide), ®Nylon 6/10, DuPont), nylon-6,12 (poly(hexamethylenedodecanediamide), ®Nylon 6/12, DuPont), nylon-6/

6,6 (poly(hexamethyleneadipamide-co-caprolactam), ®Nylon 6/66, DuPont), nylon-7 (poly-7-aminoheptanoic acid, ®Nylon 7, DuPont), nylon-7,7 (polyheptamethylenepimelamide, ®Nylon 7,7, DuPont), nylon-8 (poly-8-aminooctanoic acid, ®Nylon 8, DuPont), nylon-8,8 (polyoctamethylenesuberamide, ®Nylon 8,8, DuPont), nylon-9 (poly-9-aminononanoic acid, ®Nylon 9, DuPont), nylon-9,9 (polynonamethyleneazelamide, ®Nylon 9,9, DuPont), nylon-10 (poly-10-amino-decanoic acid, ®Nylon 10, DuPont), nylon-10,9 (poly(decamethyleneazelamide), ®Nylon 10,9, DuPont), nylon-10,10 (polydecamethylenesebacamide, ®Nylon 10,10, DuPont), nylon-11 (poly-11-aminoundecanoic acid, ®Nylon 11, DuPont), nylon-12 (polylaurolactam, ®Nylon 12, DuPont, ®Grillamid L20, Ems Chemie), aromatic polyamides derived from m-xylene, diamine, and adipic acid; polyamides prepared from hexamethylenediamine and iso- and/or terephthalic acid (polyhexamethyleneisophthalamide polyhexamethyleneterephthalamide) and, if appropriate, from an elastomer as modifier, e.g. poly-2,4,4-trimethylhexamethyleneterephthalamide or poly-m-phenyleneisophthalamide. Block copolymers of the above-mentioned polyamides with polyolefins, with olefin copolymers, with ionomers, or with chemically bonded or grafted elastomers; or with polyethers, e.g. with polyethylene glycol, polypropylene glycol, or polytetramethylene glycol. Also EPDM- or ABS-modified polyamides or copolyamides; and also polyamides condensed during processing ("RIM polyamide systems").

The inventive mixtures are preferably used in molding compositions which are further used to produce polymer moldings. Preferred process for production of polymer moldings is injection molding.

EXAMPLE 1

Comparison with the Prior Art 393 g (3 mol) of ethyldichlorophosphane were reacted with acrylic acid and methanol according to the prior art (V. K. Chajrullin, R. R. Shagidullin, Z. Obschei. Khim. 36 (1966), pp. 289-296). This gave 326 g (56% of theory) of methyl 3-(ethylmethoxyphosphinyl)propionate as colorless oil; chlorine content: 453 ppm.

EXAMPLE 2

636 g (6 mol) of sodium hypophosphite monohydrate dissolved in 860 g of water in a pressure reactor (glass autoclave) were used as initial charge. 432 g (6 mol) of acrylic acid and 73.4 g of a 7% strength hydrogen peroxide solution (2.5 mol %, based on acrylic acid) were added dropwise at from 65 to 80° C. at atmospheric pressure over a period of 2 h, from different vessels. Ethylene was then introduced into the reactor at from 80 to 105° C. by way of a reducing valve adjusted to 3 bar, until saturation had been achieved. 73.4 g of a 7% strength hydrogen peroxide solution (2.5 mol %, based on ethylene) were fed uniformly over a period of 6 h, with constant stirring (energy input of 0.8 kW/m$^3$), at ethylene pressure of from 2.5 to 2.9 bar and temperature of from 80 to 105° C.

After depressurization, the aqueous solution was acidified with about 5 g of concentrated sulfuric acid and water was removed by distillation in vacuo. Tetrahydrofuran was used to take up and extract the residue. The insoluble salts were removed by filtration. The solvent of the filtrate was removed in vacuo and the residue was recrystallized from acetone. This gave 732 g (74% of theory) of 3-(ethylhydroxyphosphinyl)propionic acid as colorless solid.

664 g (4.0 mol) of the resultant 3-(ethylhydroxyphosphinyl)propionic acid were dissolved in 400 ml of toluene at 80° C., and 402 g (3.4 mol) of 1,6-hexanediol were admixed, and the acid was esterified over a period of 4 h at from 90 to 110° C. in a distillation apparatus with water separator. Once the esterification reaction had ended, toluene was removed in vacuo. This gave 607 g (67% of theory) of 6-hydroxyhexyl 3-(ethylhydroxyphosphinyl)propionate as colorless oil; chlorine content:<0.1 ppm.

EXAMPLE 3

By analogy with example 2, 432 g (6 mol) of acrylic acid were first admixed at from 65 to 80° C. in the presence of 428 g of a 5% strength sodium peroxodisulfate solution (1.5 mol %, based on acrylic acid) with 636 g (6 mol) of sodium hypophosphite monohydrate dissolved in 860 g of water. The resultant reaction mixture was then reacted with propylene in the presence of 428 g of a 5% strength sodium peroxodisulfate solution (1.5 mol %, based on propylene). After appropriate work-up, this gave 655 g (61% of theory) of 3-(propylhydroxyphosphinyl)propionic acid as colorless solid. 540 g (3.0 mol) of the resultant 3-(propylhydroxyphosphinyl)propionic acid were dissolved in 400 ml of toluene at 85° C. and 372 g (6.0 mol) of ethylene glycol were admixed, and the acid was esterified over a period of 2 h at from 80 to 110° C. in a distillation apparatus with water separator. Once the esterification reaction had ended, toluene and excess ethylene glycol were removed in vacuo. This gave 471 g (70% of theory) of 2-hydroxyethyl 3-(propylhydroxyphosphinyl)propionate as colorless oil; chlorine content: <0.1 ppm.

EXAMPLE 4

By analogy with example 2, 468 g (6.5 mol) of methyl acrylate were first admixed at from 85 to 95° C. in the presence of 290 g of a 8% strength sodium peroxodisulfate solution (1.5 mol %, based on methyl acrylate) with 636 g (6 mol) of sodium hypophosphite monohydrate dissolved in 424 g of water. The resultant reaction mixture was then reacted with ethylene in the presence of 277 g of an 8% strength sodium peroxodisulfate solution (1.5 mol % based on ethylene). After appropriate work-up this gave 821 g (76% of theory) of methyl 3-(ethylhydroxyphosphinyl)propionate as colorless oil; chlorine content: <0.1 ppm.

EXAMPLE 5

By analogy with example 2, 781 g (6.1 mol) of butyl acrylate were first admixed at from 95 to 100° C. in the presence of 150 g of a 5% strength azoisobutyronitrile AIBN solution (0.75 mol %, based on butyl acrylate) with 636 g (6 mol) of sodium hypophosphite monohydrate dissolved in 424 g of water and 200 g of acetic acid. The resultant reaction mixture was then reacted with propylene at from 130-140° C. in the presence of 150 g of a 5% strength azoisobutyronitrile AIBN solution (0.75 mol % based on propylene). After appropriate work-up this gave 893 g (63% of theory) of butyl 3-(propylhydroxyphosphinyl)propionate as colorless oil; chlorine content: <0.1 ppm.

EXAMPLE 6

A mixture of 792 g of a 50% strength aqueous solution of hypophosphorous acid (6 mol) and 300 g of acetic acid was used as initial charge in a pressure reactor (glass autoclave). Once the reaction mixture had been heated to 115° C., butylene was introduced into the reactor by way of a reducing valve adjusted to 3 bar until saturation had been achieved. 51.6 g of a 5% strength azoisobutyronitrile AIBN solution (0.5 mol %, based on butylene) acidified with acetic acid was fed uniformly over a period of 6 h, with constant stirring, at butylene pressure of from 2.5 to 2.9 bar and temperature of from 125 to 145° C. After depressurization, 432 g (6 mol) of acrylic acid and 51.6 g of a 5% strength AIBN solution (0.5 mol %, based on acrylic acid) acidified with acetic acid were added dropwise at from 90 to 100° C. at atmospheric pressure within the period of 3 h from different feed vessels.

The solvent composed of water and acetic acid was then removed by distillation in vacuo and the residue was recrystallized from acetone/dioxane (3:1). This gave 695 g (60% of theory) of 3-(butylhydroxyphosphinyl)propionic acid as colorless solid.

582 g (3.0 mol) of the resultant 3-(butylhydroxyphosphinyl)propionic acid were dissolved in 400 ml of toluene at 90° C., and 298 g (4.8 mol) of ethylene glycol were admixed, and the acid was esterified over a period of 5 h at from 80 to 110° C. in a distillation apparatus with water separator. Once the esterification reaction had ended, the toluene was removed in vacuo. This gave 486 g (68% of theory) of 2-hydroxyethyl 3-(butylhydroxyphosphinyl)propionate as colorless oil; chlorine content: <0.1 ppm.

EXAMPLE 7

636 g (6 mol) of sodium hypophosphite monohydrate dissolved in 860 g of water were used as initial charge in a pressure reactor (glass autoclave). Once the reaction mixture had been heated to 100° C., ethylene was introduced into the reactor by way of a reducing valve adjusted to 3 bar, until saturation had been achieved. A solution of 428.4 g of a 5% strength sodium peroxodisulfate solution (1.5 mol %, based on ethylene) was fed uniformly over a period of 4 h, with constant stirring, at ethylene pressure of from 2.5 to 2.9 bar and temperature of from 100 to 130° C. After depressurization, 602 g (7 mol) of methacrylic acid and 500 g of a 5% strength sodium peroxodisulfate solution (1.5 mol %, based on methacrylic acid) were added dropwise within a period of 1 h at from 90 to 100° C. at atmospheric pressure, from different feed vessels.

The aqueous solution was then acidified with about 5 g of concentrated sulfuric acid and water was removed by distillation in vacuo. Tetrahydrofuran was used to take up and extract the residue. The insoluble salts were removed by filtration. The solvent of the filtrate was removed in vacuo and the residue was recrystallized from acetone. This gave 591 g (55% of theory) of 3-(ethylhydroxyphosphinyl)-2-methylpropionic acid as colorless solid.

540 g (3.0 mol) of the resultant 3-(ethylhydroxyphosphinyl)-2-methylpropionic acid were dissolved in 400 ml of toluene at 80° C. and 297 g (3.3 mol) of 1,4-butanediol were admixed, and the acid was esterified over a period of 4 h at from 80 to 110° C. in a distillation apparatus with water separator. Once the esterification reaction had ended, the toluene was removed in vacuo. This gave 507 g (67% of theory) of 4-hydroxybutyl 3-(ethylhydroxyphosphinyl)-2-methylpropionate as colorless oil; chlorine content: <0.1 ppm.

EXAMPLE 8

636 g (6 mol) of sodium hypophosphite monohydrate dissolved in 860 g of water were used as initial charge in a pressure reactor (glass autoclave). Once the reaction mixture had been heated to 100° C., ethylene was introduced into the reactor by way of a reducing valve adjusted to 3 bar, until saturation had been achieved. A solution of 91.86 g of a 7% strength hydrogen peroxide solution (3.0 mol %, based on ethylene) was fed uniformly over a period of 4 h, with constant stirring, at ethylene pressure of from 2.5 to 2.9 bar and temperature of from 60 to 70° C. After depressurization, 731.5 g (6.3 mol) of hydroxy ethyl acrylate and 91.86 g of a 7% strength hydrogen peroxide solution (3.0 mol %, based on hydroxyethyl acrylate) were added dropwise at from 65 to 75° C. at atmospheric pressure within a period of 2 h, from different feed vessels.

The aqueous solution was then acidified with about 5 g of concentrated sulfuric acid and water was removed by distillation in vacuo. Tetrahydrofuran was used to take up and extract the residue. The insoluble salts were removed by filtration. The solvent of the filtrate was removed in vacuo. This gave 920 g (73% of theory) of 2-hydroxyethyl 3-(ethylhydroxyphosphinyl)propionate as colorless oil; chlorine content: <0.1 ppm.

EXAMPLE 9

By analogy with example 7, propylene was first admixed at from 140 to 145° C. in the presence of 609 g of a 5% strength sodium peroxodisulfate solution (2.0 mol %, based on propylene) with 636 g (6 mol) of sodium hypophosphite monohydrate dissolved in 860 g of water. The resultant reaction mixture was then reacted at from 95 to 100° C. with 893.4 g (6.2 mol) of 2-hydroxypropyl methacrylate in the presence of 590 g of a 5% strength sodium peroxodisulfate solution (2.0 mol % based on 2-hydroxypropyl methacrylate). After appropriate acid work-up this gave 802 g (53% of theory) of 2-hydroxypropyl 3-(propylhydroxyphosphinyl)-2-methylpropionate as colorless oil; chlorine content: <0.1 ppm.

EXAMPLE 10

By analogy with example 7, ethylene was first admixed at from 120 to 135° C. in the presence of 590 g of a 5% strength sodium peroxodisulfate solution (2.0 mol %, based on ethylene) with 636 g (6 mol) of sodium hypophosphite monohydrate dissolved in 860 g of water. The resultant reaction mixture was then reacted with 782.4 g (6.2 mol) of allyl methacrylate in the presence of 590 g of a 5% strength sodium peroxodisulfate solution (2.0 mol % based on allyl methacrylate). After appropriate acid work-up this gave 740 g (56% of theory) of allyl 3-(ethylhydroxyphosphinyl)-2-methylpropionate as colorless oil; chlorine content: <0.1 ppm.

EXAMPLE 11

636 g (6 mol) of sodium hypophosphite monohydrate dissolved in 860 g of water were used as initial charge in a pressure reactor (glass autoclave). Once the reaction mixture had been heated to 120° C., 1-hexene was introduced into the reactor by way of a reducing valve adjusted to 3 bar, until saturation had been achieved. 142.8 g of a 5% strength sodium peroxodisulfate solution (1.5 mol %, based on 1-hexene) were fed uniformly over a period of 1 h, with constant stirring (energy input of 1.1 kW/m$^3$) at hexene pressure of from 2.5 to 2.9 bar and temperature of from 120 to 140° C. After depressurization, 432 g (6 mol) of acrylic acid and 428 g of a 5% strength sodium peroxodisulfate solution (1.5 mol %, based on acrylic acid) were added dropwise at from 90 to 100° C. at atmospheric pressure within a period of 2 h, from different feed vessels. Once the reaction mixture had been heated to 120° C., 1-hexene was again introduced into the reactor by way of a reducing valve adjusted to 3 bar, until saturation had been achieved. 428 g of a 5% strength sodium peroxodisulfate solution (1.5 mol %, based on 1-hexene) were fed uniformly over a period of 6 h, with constant stirring, at hexene pressure of from 2.5 to 2.9 bar and temperature of from 120 to 140° C.

The aqueous solution was then acidified with about 5 g of concentrated sulfuric acid, and water was removed by distillation in vacuo. Tetrahydrofuran was used to take up and extract the residue. The insoluble salts were removed by filtration. The solvent of the filtrate was removed in vacuo and the residue was recrystallized from amyl alcohol/acetone (2:1). This gave 769 g (60% of theory) of 3-(hexylhydroxyphosphinyl)propionic acid as colorless solid.

667 g (3.0 mol) of the resultant 3-(hexylhydroxyphosphinyl)propionic acid were dissolved in 400 ml of toluene at 80° C. and 228 g (3.0 mol) of 1,3-propanediol were admixed, and the acid was esterified over a period of 5 h at from 80 to 110° C. in a distillation apparatus with water separator. Once the esterification reaction had ended, the toluene was removed in vacuo. This gave 547 g (65% of theory) of 3-hydroxypropyl 3-(hexylhydroxyphosphinyl)propionate as colorless oil; chlorine content: <0.1 ppm.

EXAMPLE 12

636 g (6 mol) of sodium hypophosphite monohydrate and 15 g of concentrated sulfuric acid were dissolved in 860 g of water. By analogy with example 11, the mixture was first reacted with propylene within a period of 2 h in the presence of 214 g of a 5% strength sodium peroxodisulfate solution (1.5 mol %, based on propylene). 516.5 g (6 mol) of methyl acrylate were then admixed in the presence of 428 g of a 5% strength sodium peroxodisulfate solution (1.5 mol %, based on methyl acrylate), and then propylene was again added in the presence of 214 g of a 5% strength sodium peroxodisulfate solution.

The resultant aqueous solution was acidified with about 5 g of concentrated sulfuric acid and water was removed in vacuo. Tetrahydrofuran was used to take up and extract the residue. The insoluble salts were removed by filtration, and the solvent of the filtrate was removed in vacuo. This gave 850 g (73% of theory) of methyl 3-(propylhydroxyphosphinyl) propionate as colorless oil; chlorine content: <0.1 ppm.

EXAMPLE 13

636 g (6 mol) of sodium hypophosphite monohydrate and 15 g of concentrated sulfuric acid dissolved in 860 g of water were used as initial charge in a pressure reactor (glass autoclave). 216 g (3 mol) of acrylic acid and 36.5 g of a 7% strength hydrogen peroxide solution (2.5 mol %, based on acrylic acid) were then added dropwise at from 75 to 90° C. at atmospheric pressure within a period of 1 h, from different feed vessels. Ethylene was then introduced into the reactor at from 80 to 105° C. by way of a reducing valve adjusted to 3 bar, until saturation had been achieved. 73 g of a 7% strength hydrogen peroxide solution (2.5 mol %, based on ethylene) were fed uniformly over a period of 4 h, with constant stirring, at ethylene pressure of from 2.5 to 2.9 bar and temperature of from 80 to 105° C. After depressurization, 216 g (3 mol) of acrylic acid and 36.5 g of a 7% strength hydrogen peroxide solution (2.5 mol %, based on acrylic acid) were again added dropwise within a period of 1 h at from 75 to 90° C., from different feed vessels. Water was then removed by distillation in vacuo. Tetrahydrofuran was used to take up and extract the residue. The insoluble salts were removed by filtration. The solvent of the filtrate was removed in vacuo and the residue was recrystallized from acetone. This gave 772 g (78% of theory) of 3-(ethylhydroxyphosphinyl)propionic acid as colorless solid.

498 g (3.0 mol) of the resultant 3-(ethylhydroxyphosphinyl)propionic acid were dissolved in 400 ml of toluene at 80° C., and 276 g (3.0 mol) of glycerol were admixed, and the acid was esterified over a period of 6 h at from 80 to 110° C. in a distillation apparatus with water separator. Once the esterification reaction had ended, the toluene was removed in vacuo. This gave 555 g (77% of theory) of 2,3-dihydroxypropyl 3-(ethylhydroxyphosphinyl)propionate as colorless oil; chlorine content: <0.1 ppm.

EXAMPLE 14

Using a method similar to that of example 13, 390 g (3 mol) of hydroxypropyl acrylate were first admixed in the presence of 142.8 g of a 5% strength sodium peroxodisulfate solution (1.0 mol %, based on acrylic acid) with 636 g (6 mol) of sodium hypophosphite monohydrate dissolved in 1181 g of water. The resultant reaction mixture was then reacted with propylene at from 135 to 140° C. in the presence of 290.4 g of a 5% strength sodium peroxodisulfate solution (1.0 mol %, based on propylene). The autoclave was then depressurized and a further 403 g (3.1 mol) of hydroxypropyl acrylate were then fed at from 95 to 100° C. in the presence of 147.6 g of a 5% strength sodium peroxodisulfate solution (1.0 mol %, based on acrylic ester).

After appropriate acidic work-up, this gave 867 g (65% of theory) of 2-hydroxypropyl 3-(propylhydroxyphosphinyl) propionate as colorless oil; chlorine content: <0.1 ppm.

EXAMPLE 15

A mixture of 792 g of a 50% strength aqueous solution of hypophosphorous acid (6 mol) and 300 g of acetic acid was used as initial charge in a pressure reactor (glass autoclave). Once the reaction mixture had been heated to 115° C., ethylene was introduced into the reactor by way of a reducing valve adjusted to 3 bar, until saturation had been achieved. 49.3 g of a 5% strength solution (0.5 mol %, based on ethylene) of azoisobutyronitrile AIBN acidified with acetic acid were fed uniformly over a period of 2 h, with constant stirring, at ethylene pressure of from 2.5 to 2.9 bar and temperature of from 120 to 140° C. After depressurization, 258.3 g (3 mol) of methyl acrylate and 49.3 g of a 5% strength solution (0.5 mol %, based on methyl acrylate) of AIBN acidified with acetic acid were added dropwise at from 90 to 110° C. at atmospheric pressure within a period of 1 h, from different feed vessels.

The following amounts were accordingly fed in alternation:
in the presence of ethylene, 29.6 g of 5% strength AIBN solution acidified with acetic acid,
155 g of methyl acrylate and 29.6 g of 5% strength AIBN solution acidified with acetic acid,
in the presence of ethylene, 19.7 g of 5% strength AIBN solution acidified with acetic acid,
103.3 g of methyl acrylate and 19.7 g of 5% strength AIBN solution acidified with acetic acid,
in the presence of ethylene, 29.6 g of 5% strength AIBN solution acidified with acetic acid.

The solvent composed of water and acetic acid was then removed by distillation in vacuo. This gave 743 g (75% of theory) of methyl 3-(ethylhydroxyphosphinyl)propionate as colorless oil; chlorine content: <0.1 ppm.

EXAMPLE 16

By analogy with example 15, a mixture of 636 g of sodium hypophosphite monohydrate dissolved in 1181 g of water was used as initial charge in a pressure reactor (glass autoclave) and 49.3 g of a 5% strength azoisobutyronitrile AIBN solution (0.5 mol %, based on ethylene) acidified with acetic acid was fed uniformly at ethylene pressure of from 2.5 to 2.9 bar and temperature of from 120 to 140° C. After depressurization, 348.3 g (3 mol) of hydroxyethyl acrylate and 49.3 g of a 5% strength AIBN solution (0.5 mol %, based on hydroxyethyl acrylate) acidified with acetic acid were added dropwise at from 90 to 110° C. at atmospheric pressure within a period of 1 h, from different feed vessels.

The following amounts were accordingly fed in alternation:

in the presence of ethylene, 29.6 g of 5% strength AIBN solution acidified with acetic acid,
208.0 g of hydroxyethyl acrylate and 29.6 g of 5% strength AIBN solution acidified with acetic acid,
in the presence of ethylene, 19.7 g of 5% strength AIBN solution acidified with acetic acid,
139.3 g of hydroxyethyl acrylate and 19.7 g of 5% strength AIBN solution acidified with acetic acid,
in the presence of ethylene, 29.6 g of 5% strength AIBN solution acidified with acetic acid.

The solvent composed of water and acetic acid was then removed by distillation in vacuo. This gave 983 g (78% of theory) of 2-hydroxyethyl 3-(ethylhydroxyphosphinyl)propionate as colorless oil; chlorine content: <0.1 ppm.

EXAMPLE 17

636 g (6 mol) of sodium hypophosphite monohydrate dissolved in 860 g of water were used as initial charge in a pressure reactor (glass autoclave). Once the reaction mixture had been heated to 100° C., ethylene was introduced into the reactor by way of a reducing valve adjusted to 3 bar, until saturation had been achieved. 428.4 g of a 5% strength sodium peroxodisulfate solution (1.5 mol %, based on ethylene) were fed uniformly over a period of 4 h, with constant stirring, at ethylene pressure of from 2.5 to 2.9 bar and temperature of from 100 to 130° C. After depressurization, 216 g (3 mol) of acrylic acid and 214.2 g of a 5% strength sodium peroxodisulfate solution (1.5 mol %, based on acrylic acid) were added dropwise at from 90 to 100° C. at atmospheric pressure within a period of 1 h, from different feed vessels.

The two steps were repeated at appropriate temperatures by again adjusting to an ethylene pressure of from 2.5 to 2.9 bar and then metering 214.2 g of a 5% strength sodium peroxodisulfate solution over a period of 2 h. 216 g (3 mol) of acrylic acid were then again admixed with the reaction mixture in the presence of 214.2 g of a 5% strength sodium peroxodisulfate solution.

The aqueous solution was then acidified with about 5 g of concentrated sulfuric acid and water was removed by distillation in vacuo. Tetrahydrofuran was used to take up and extract the residue. The insoluble salts were removed by filtration. The solvent of the filtrate was removed in vacuo and the residue was recrystallized from acetone. This gave 752 g (76% of theory) of 3-(ethylhydroxyphosphinyl)propionic acid as colorless solid. 664 g (4.0 mol) of the resultant 3-(ethylhydroxyphosphinyl)propionic acid were dissolved in 400 ml of toluene at 90° C., and 248 g (4.0 mol) of ethylene glycol were admixed, and the acid was esterified over a period of 5 h at from 80 to 110° C. in a distillation apparatus with water separator. After the esterification reaction had ended, toluene was removed in vacuo. This gave 714 g (85% of theory) of 2-hydroxyethyl 3-(ethylhydroxyphosphinyl)propionate as colorless oil; chlorine content: <0.1 ppm.

EXAMPLE 18

Ethylation 636 g (6 mol) of sodium hypophosphite monohydrate dissolved in 860 g of water were used as initial charge in a pressure reactor (glass autoclave). Once the reaction mixture had been heated to 100° C., ethylene was introduced into the reactor by way of a reducing valve adjusted to 3 bar, until saturation had been achieved. 428.4 g of a 5% strength sodium peroxodisulfate solution (1.5 mol %, based on ethylene) were fed uniformly over a period of 4 h, with constant stirring, at ethylene pressure of from 2.5 to 2.9 bar and temperature of from 100 to 130° C.

2. Esterification

The aqueous reaction solution was acidified with about 5 g of concentrated sulfuric acid and water was removed by distillation in vacuo. 700 g of butanol were used to take up and extract the residue. The insoluble salts were removed by filtration. A further 1530 g of butanol were admixed with the filtrate and the mixture was heated at atmospheric pressure under conditions giving water separation. Once esterification had ended, butanol was removed in vacuo and the residue was distilled by way of a Vigreux column in vacuo. This gave 586 g (65% of theory) of n-butyl ethanephosphonite as colorless liquid.

3. Acrylic Acid Addition Reaction 450 g (3 mol) of n-butyl ethanephosphonite obtained by the above process and 385 g (3 mol) of n-butyl acrylate were used as initial charge in a 1 l five-necked flask with thermometer, reflux condenser, high-performance stirrer, and dropping funnel. 15 ml of sodium butoxide (30%) were added dropwise, with stirring, at a rate such that the reaction temperature established was at most 120° C. The mixture was then heated for a further 20 min at 80° C., with stirring. The resultant crude product was distilled in vacuo. This gave 751 g (90% of theory) of butyl 3-(ethyl-n-butoxyphosphinyl)propionate as colorless liquid; chlorine content: <0.1 ppm.

EXAMPLE 19

By analogy with example 18, starting from sodium hypophosphite monohydrate, 451 g (3 mol) of n-butyl ethanephosphonite are prepared and reacted with 416 g (3.2 mol) of hydroxyethyl methacrylate. This gave 551 g (82% of theory) of 2-hydroxyethyl 3-(ethyl-n-butoxyphosphinyl)isobutyrate as colorless liquid; chlorine content: <0.1 ppm.

EXAMPLE 20

By analogy with example 18, 556 g (2 mol) of dibutyl carboxyethylethylphosphinate are prepared and used as initial charge in a 1 l five-necked flask with thermometer, reflux condenser, high-performance stirrer, and dropping funnel. 500 ml of water are fed at 160° C. within a period of 4 h, and a butanol-water mixture is removed by distillation. The solid residue was recrystallized from acetone. This gave 305 g (92% of theory) of 3-(ethylhydroxyphosphinyl)propionic acid as colorless solid.

498 g (3.0 mol) of the resultant 3-(ethylhydroxyphosphinyl)propionic acid were dissolved in 400 ml of toluene at 85° C., and 335 g (5.4 mol) of ethylene glycol were admixed, and the acid was esterified over a period of 2 h at from 80 to 110° C. in a distillation apparatus with water separator. Once the esterification reaction had ended, toluene and excess ethylene glycol were removed in vacuo. This gave 460 g (73% of theory) of 2-hydroxyethyl 3-(ethylhydroxyphosphinyl)propionate as colorless oil; chlorine content: <0.1 ppm.

EXAMPLE 21

Ethylation 636 g (6 mol) of sodium hypophosphite monohydrate dissolved in 860 g of water were used as initial charge in a pressure reactor (glass autoclave). Once the reaction mixture had been heated to 100° C., ethylene was introduced into the reactor by way of a reducing valve adjusted to 3 bar, until saturation had been achieved. 428.4 g of a 5% strength sodium peroxodisulfate solution (1.5 mol %, based on ethylene) were fed uniformly over a period of 4 h, with constant stirring, at ethylene pressure of from 2.5 to 2.9 bar and temperature of from 100 to 130° C.

2. Esterification

The aqueous reaction solution was acidified with about 5 g of concentrated sulfuric acid and water was removed by distillation in vacuo. 600 g of methanol were used to take up and extract the residue. The insoluble salts were removed by filtration. A further 1800 g of chloroform were admixed with the filtrate and the mixture was heated at atmospheric pressure under reflux. After the esterification reaction had ended, the organic phase was removed. The extractant comprising methanol and $CHCl_3$ is removed by distillation in vacuo and the residue is distilled in vacuo by way of a Vigreux column. This gave 460 g (71% of theory) of methyl ethanephosphonite as colorless liquid.

3. Acrylic Acid Addition Reaction 324 g (3 mol) of methyl ethanephosphonite obtained by the above process and 216 g (3 mol) of methyl acrylate were used as initial charge in a 1 l five-necked flask with thermometer, reflux condenser, high-performance stirrer, and dropping funnel. 15 ml of sodium methylate (30%) were added dropwise to the mixture, with stirring, at a rate such that the resultant reaction temperature was at most 60° C. The mixture was then heated for a further 20 min at 65° C., with stirring. The resultant crude product was distilled in vacuo. This gave 536 g (92% of theory) of methyl 3-(ethylmethoxyphosphinyl)propionate as colorless liquid; chlorine content: <0.1 ppm.

EXAMPLE 22

Corrosion Test with Product from Example 1

A corrosion test was carried out with the methyl 3-(ethylmethoxyphosphinyl)propionate (chlorine content: 453 ppm) obtained in example 1. Ablation via corrosion was 0.23 mm/a using 1.4571 steel at 225° C. in the full immersion test.

EXAMPLE 23

Corrosion Test with Product from Example 21

A corrosion test was carried out with the methyl 3-(ethylmethoxyphosphinyl) propionate (chlorine content: <0.1 ppm) obtained from example 21. Ablation via corrosion was <0.01 mm/a using 1.4571 steel at 250° C. in the full immersion test.

This corrosion rate is considerably more advantageous than in example 22. The corrosion test provides evidence of the suitability of the flame retardant for use during processing of flame retardants, of flame-retardant polymer molding compositions, and/or of flame-retardant polymer moldings.

EXAMPLE 24

Polyester Moldings and Fire Tests

Dimethyl terephthalate, ethylene glycol, and 2-hydroxyethyl 3-ethylhydroxyphosphinyl)propionate (from example 8) in a ratio by weight of 1000:800:90 were polymerized under the conventional conditions in the presence of zinc acetate and antimony(III) oxide. The melt obtained (phosphorus content: 0.7%) was used to injection-mold specimens of thickness 1.6 mm for measurement of oxygen index (LOI) to ISO 4589-2 and also for the UL 94 (Underwriter Laboratories) fire test.

The test specimens thus produced gave an LOI of 44% $O_2$ and complied with fire class V-0 to UL 94. Corresponding test specimens without 2-hydroxyethyl 3-(ethylhydroxyphosphinyl)propionate gave an LOI of only 31% $O_2$ and complied only with fire class V-2 to UL 94. The polyester molding comprising 3-(ethylhydroxyphosphinyl)propionic acid therefore clearly exhibits flame-retardant properties.

The invention claimed is:
1. A process for preparation of a composition comprising:
A) from 98 to 100% by weight of at least one monocarboxy-functionalized dialkylphosphinic ester of the formula (I)

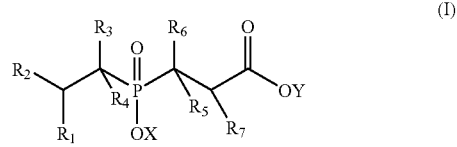

wherein $R_1$, $R_2$, $R_3$, $R_4$, $R_5$, $R_6$, and $R_7$ are identical or different and independently of one another, are H, methyl, ethyl, n-propyl, isopropyl, n-butyl, isobutyl, tert-butyl, or phenyl, Y is methyl, ethyl, n-propyl, isopropyl, n-butyl, isobutyl, tert-butyl, phenyl, 2-hydroxyethyl, 2,3-dihydroxypropyl, 2-hydroxypropyl, 3-hydroxypropyl, 4-hydroxybutyl, 3-hydroxybutyl, 2-hydroxybutyl, 6-hydroxyhexyl, allyl, or glycerol, X is H, Li, Na, K or $NH_4$, or X is defined as for Y, and then X and Y are two identical radicals or two different radicals of the above organic radicals, and B) from 0 to 2% by weight of at least one halogen, wherein the at least one halogen is a chemical compound in which atoms of the 7th main group of the periodic table of elements are present and have chemical bonding to carbon or to phosphorus or salts containing halide anions, where the entirety of the components always amounts to 100% by weight, comprising the step of reacting hypophosphorous acid or a salt thereof (component C) of the formula II

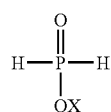

wherein X is H, Na, K, or NH$_4$ in the presence of at least one free-radical initiator with at least one α,β-unsaturated carboxylic acid derivative (component D) of the formula III,

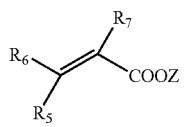

wherein Z is C$_{1-18}$-alkyl or C$_{6-18}$-aryl or is Y, or with at least one α,β-unsaturated carboxylic acid (component D') of the formula IV

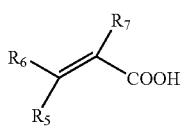

and with at least one olefin (component E) of the formula V

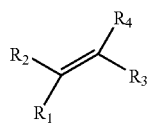

wherein R$_1$, R$_2$, R$_3$, R$_4$, R$_5$, R$_6$, and R$_7$ are defined in the formulae III, IV, and V as in formula I, and wherein when formula IV is used an esterification step with Y—OH follows.

2. The process as claimed in claim 1, wherein, in a step 1, component C is reacted in the presence of the at least one free-radical initiator with component E to give an alkylphosphorous acid and, in step 2, the resultant reaction solution is esterified with an alcohol M-OH to produce phosphous ester in the resultant reaction mixture, and the phosphonous ester is removed by distillation and, in a step 3, the resultant reaction mixture is reacted in the presence of the at least one free-radical initiator or of a basic initiator with component D to give the at least one monocarboxy-functionalized dialkylphosphinic ester.

3. The process as claimed in claim 1, wherein, in a step 1, component C is reacted in the presence of the at least free-radical initiator with component E to give an alkylphosphonous acid and, in step 2, the resultant reaction solution is esterified with an alcohol M-OH to produce phosphonous ester in the resultant reaction solution and the phosphonous ester is removed by distillation and, in a step 3, the resultant reaction mixture is reacted in the presence of the at least one free-radical initiator or of a basic initiator with component D' to give the at least one monocarboxy-functionalized dialkylphosphinic ester, where X=alkyl, Y=H, and then, in a step 4, the dialkylphosphinic ester is esterified with an alcohol Y—OH at the carboxy function, giving a monocarboxy-functionalized dialkylphosphinic ester A.

4. The process as claimed in claim 3, wherein, in step 2, the alkylphosphonous acid is directly esterified with a linear or branched alcohol of the formula M-OH, where M is a linear or branched alkyl radical having from 1 to 10 carbon atoms.

5. The process as claimed in claim 4, wherein the alcohol M-OH is n-butanol, isobutanol, or ethylhexanol.

6. The process as claimed in claim 1, wherein component C is the ammonium or sodium salt of hypophosphorous acid.

7. The process as claimed in claim 1, wherein the at least one free radical initiator is a free-radical, anionic, cationic, or photochemical initiator.

8. The process as claimed in claim 1, wherein the at least one free radical initiator is a peroxide-forming compound, a peroxo compound, an azo compound or a mixture thereof.

9. The process as claimed in claim 1, wherein the at least one α,β-unsaturated carboxylic acid is acrylic acid, methyl acrylate, ethyl acrylate, methacrylic acid, hydroxyethyl acrylate, crotonic acid, ethyl crotonate, tiglic acid (trans-2,3-dimethylacrylic acid), (trans-)2-pentenoic acid or a mixture thereof.

10. The process as claimed in claim 1, wherein the at least one olefin (component E) is ethylene, propylene, n-butene, and/or isobutene, 1-hexene, 1-heptene, and/or 1-octene; allyl alcohol, allylamine, allylbenzene, allylanisole, styrene, α-methylstyrene, 4-methylstyrene, vinyl acetate or a mixture thereof.

11. The process as claimed in claim 1, wherein the reaction of component C with components D, E or both takes place at a temperature of from 50 to 150° C.

12. A process for preparation of a composition comprising:
A) from 98 to 100% by weight of at least one monocarboxy-functionalized dialkylphosphinic ester of the formula (I)

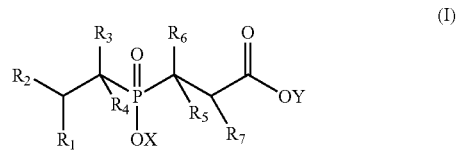

wherein R$_1$, R$_2$, R$_3$, R$_4$, R$_5$, R$_6$, and R$_7$ are identical or different and, independently of one another, are H, methyl, ethyl, n-propyl, isopropyl, n-butyl, isobutyl, tert-butyl, or phenyl, Y is methyl, ethyl, n-propyl, isopropyl, n-butyl, isobutyl, tert-butyl, phenyl, 2-hydroxyethyl, 2,3-dihydroxypropyl, 2-hydroxypropyl, 3-hydroxypropyl, 4-hydroxybutyl, 3-hydroxybutyl, 2-hydroxybutyl, 6-hydroxyhexyl, allyl, or glycerol, X is H, Li, Na, K or NH$_4$, or X is defined as for Y, and then X and Y are two identical radicals or two different radicals of the above organic radicals, and B) from 0 to 2% by weight of at least one halogen, wherein the at least one halogen is a chemical compound in which atoms of the 7th main group of the periodic table of elements are present and have chemical bonding to carbon or to phosphorus or salts containing halide anions, where the entirety of the components always amounts to 100% by weight comprising the steps of reacting a hypophosphorous acid or a salt thereof (component C) of the formula II

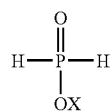

wherein X is H, Na, K, or NH₄, with a ketone to give 1-hydroxy-1-dialkylphosphinate, reacting the 1-hydroxy-1-dialkylphosphinate, in the presence of at least one free-radical initiator with at least one α,β-unsaturated carboxylic acid derivative (component D) of the formula III,

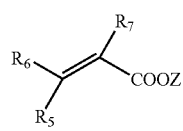

wherein Z is $C_{1-18}$-alkyl or $C_{6-18}$-aryl or is Y, removing the ketone to form a resultant reaction mixture, and reacting the resultant reaction mixture, in the presence of the at least one free-radical initiator with at least one olefin (component E) of the formula V

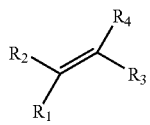

wherein $R_1$, $R_2$, $R_3$, $R_4$, $R_5$, $R_6$, and $R_7$ are defined in the formulae III, IV, and V as in formula I.

13. A process for preparation of a composition comprising:
A) from 98 to 100% by weight of at least one monocarboxy-functionalized dialkylphosphinic ester of the formula (I)

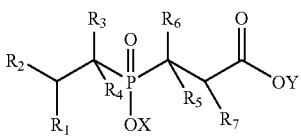

wherein $R_1$, $R_2$, $R_3$, $R_4$, $R_5$, $R_6$, and $R_7$ are identical or different and, independently of one another, are H, methyl, ethyl, n-propyl, isopropyl, n-butyl, isobutyl, tert-butyl, or phenyl,
Y is methyl, ethyl, n-propyl, isopropyl, n-butyl, isobutyl, tert-butyl, phenyl, 2-hydroxyethyl, 2,3-dihydroxypropyl, 2-hydroxypropyl, 3-hydroxypropyl, 4-hydroxybutyl, 3-hydroxybutyl, 2-hydroxybutyl, 6-hydroxyhexyl, allyl, or glycerol,
X is H, Li, Na, K or NH₄,
or X is defined as for Y, and then X and Y are two identical radicals or two different radicals of the above organic radicals, and
B) from 0 to 2% by weight of at least one halogen, wherein the at least one halogen is a chemical compound in which atoms of the 7th main group of the periodic table of elements are present and have chemical bonding to carbon or to phosphorus or salts containing halide anions, where the entirety of the components always amounts to 100% by weight, comprising the steps of reacting a hypophosphorous acid or a salt thereof (component C) of the formula II

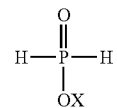

wherein X is H, Na, K, or NH₄ with a ketone to give 1-hydroxy-1-dialkylphosphinate, reacting the 1-hydroxy-1-dialkylphosphinate in the presence of at least one free-radical initiator with at least one α,β-unsaturated carboxylic acid (component D') of the formula IV

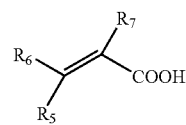

removing the ketone to form a resultant reaction mixture, and reacting the resultant reaction mixture, in the presence of the at least one free-radical initiator with at least one olefin (component E) of the formula V

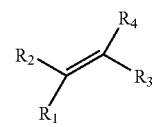

wherein $R_1$, $R_2$, $R_3$, $R_4$, $R_5$, $R_6$, and $R_7$ are defined in the formulae III, IV, and V as in formula I to form the monocarboxy-functionalized dialkylphosphinic acid, where Y=H; and reacting the monocarboxy-functionalized dialkylphosphinic acid with an alcohol YOH to give the monocarboxy-functionalized dialkylphosphinic ester.

14. A process for preparation of a composition comprising:
A) from 98 to 100% by weight of at least one monocarboxy-functionalized dialkylphosphinic ester of the formula (I)

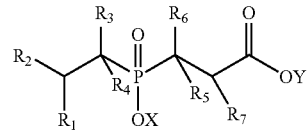

wherein $R_1$, $R_2$, $R_3$, $R_4$, $R_5$, $R_6$, and $R_7$ are identical or different and, independently of one another, are H, methyl, ethyl, n-propyl, isopropyl, n-butyl, isobutyl, tert-butyl, or phenyl,
Y is methyl, ethyl, n-propyl, isopropyl, n-butyl, isobutyl, tert-butyl, phenyl, 2-hydroxyethyl, 2,3-dihydroxypropyl, 2-hydroxypropyl, 3-hydroxypropyl, 4-hydroxybutyl, 3-hydroxybutyl, 2-hydroxybutyl, 6-hydroxyhexyl, allyl, or glycerol,
X is H, Li, Na, K or NH₄,
or X is defined as for Y, and then X and Y are two identical radicals or two different radicals of the above organic radicals, and B) from 0 to 2% by weight of at least one halogen, wherein the at least one halogen is a chemical compound in which atoms of the 7th main group of the periodic table of elements are present and have chemical bonding to carbon or to phosphorus or salts containing halide anions, where the entirety of the components always amounts to 100% by weight, comprising the steps of reacting hypophosphorous acid or a salt thereof (component C) of the formula II

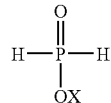
II wherein X is H, Na, K, or $NH_4$ with acetone to give 1-hydroxy-1-methylethylphosphinate, reacting the 1-hydroxy-1-methylethyl-phosphinate, in the presence of at least one free-radical initiator with at least one olefin (component E) of the formula V

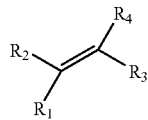
V wherein $R_1$, $R_2$, $R_3$, $R_4$, $R_5$, $R_6$, and $R_7$ are defined in the formulae III, IV, and V as in formula I, removing the acetone to form a resultant reaction mixtures, and reacting the resultant reaction mixture, in the presence of the at least one free-radical initiator with at least one α,β-unsaturated carboxylic acid derivative (component D) of the formula III,

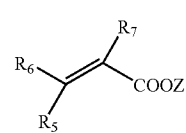
III wherein Z is $C_{1-18}$-alkyl or $C_{6-18}$-aryl or is Y, or with at least one α,β-unsaturated carboxylic acid (component D') of the formula IV

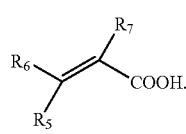
IV

15. The process as claimed in claim 14, wherein, after the reaction with component D', the monocarboxy-functionalized dialkylphosphinic acid thus obtained, wherein Y=H is reacted with an alcohol YOH to give the monocarboxy-functionalized dialkylphosphinic ester.

* * * * *